United States Patent
Lugosi et al.

(10) Patent No.: US 11,318,328 B2
(45) Date of Patent: *May 3, 2022

(54) PRESENTING A SEQUENCE OF IMAGES ASSOCIATED WITH A MOTION MODEL

(71) Applicant: ACCURAY INCORPORATED, Sunnyvale, CA (US)

(72) Inventors: Kolos Lugosi, Livermore, CA (US); Kyle Nethery-Pavelchak, San Jose, CA (US); Matthew Core, San Jose, CA (US); Calvin Maurer, San Jose, CA (US); Petr Jordan, Redwood City, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/056,221

(22) Filed: Aug. 6, 2018

(65) Prior Publication Data
US 2018/0345041 A1  Dec. 6, 2018

Related U.S. Application Data

(63) Continuation of application No. 15/005,985, filed on Jan. 25, 2016, now Pat. No. 10,065,049.

(51) Int. Cl.
*A61N 5/10* (2006.01)
*G06T 7/00* (2017.01)
(Continued)

(52) U.S. Cl.
CPC ............ *A61N 5/1049* (2013.01); *A61B 6/463* (2013.01); *A61B 6/465* (2013.01); *A61B 6/5235* (2013.01);
(Continued)

(58) Field of Classification Search
CPC ...... A61B 2034/107; A61B 2034/2055; A61B 2034/254; A61B 2090/364;
(Continued)

(56) References Cited

U.S. PATENT DOCUMENTS 6,937,696 B1  8/2005  Moustafavi
2005/0020917 A1  1/2005  Scherch
(Continued)

FOREIGN PATENT DOCUMENTS

WO  2016000777  1/2016

OTHER PUBLICATIONS

Mu et al., "A Probabilistic Framework Based on Hidden Markov Model for Fiducial Identification in Image-Guided Radiation Treatments", IEEE Transactions on Medical Images, vol. 27, No. 9, Sep. 2008, 13 pages, 0278-00062, Accuray Incorporated, Sunnyvale, CA 94089, USA.
(Continued)

*Primary Examiner* — Manuchehr Rahmjoo
(74) *Attorney, Agent, or Firm* — Womble Bond Dickinson (US) LLP

(57) ABSTRACT

Images that are associated with an identification of a tracking target of a patient to receive radiation treatment may be received. The images may be sorted into a sequence based on a motion of the patient. The sorted images may be provided via a graphical user interface. The sequence of the sorted images that are based on the motion of the patient may be provided.

12 Claims, 17 Drawing Sheets

(51) Int. Cl.

| | |
|---|---|
| *G06T 7/20* | (2017.01) |
| *G06T 11/00* | (2006.01) |
| *A61B 6/00* | (2006.01) |
| *G06T 19/00* | (2011.01) |
| *A61B 34/00* | (2016.01) |
| *G16H 20/40* | (2018.01) |
| *G16H 30/20* | (2018.01) |
| *G16Z 99/00* | (2019.01) |
| *G06T 17/00* | (2006.01) |
| *G06T 19/20* | (2011.01) |
| *G06T 7/38* | (2017.01) |
| *G06T 7/246* | (2017.01) |
| *G16H 40/63* | (2018.01) |
| *G16H 30/40* | (2018.01) |
| *A61B 6/02* | (2006.01) |
| *A61B 6/03* | (2006.01) |
| *A61B 6/12* | (2006.01) |
| *A61B 5/08* | (2006.01) |
| *A61B 5/11* | (2006.01) |
| *A61B 5/113* | (2006.01) |
| *A61B 90/00* | (2016.01) |
| *A61B 34/20* | (2016.01) |
| *A61B 34/10* | (2016.01) |

(52) U.S. Cl.
CPC .......... *A61B 6/5288* (2013.01); *A61B 6/5294* (2013.01); *A61B 34/25* (2016.02); *A61N 5/1037* (2013.01); *A61N 5/1067* (2013.01); *G06T 7/0016* (2013.01); *G06T 7/20* (2013.01); *G06T 7/251* (2017.01); *G06T 7/38* (2017.01); *G06T 11/008* (2013.01); *G06T 17/00* (2013.01); *G06T 19/00* (2013.01); *G06T 19/20* (2013.01); *G16H 20/40* (2018.01); *G16H 30/20* (2018.01); *G16H 30/40* (2018.01); *G16H 40/63* (2018.01); *G16Z 99/00* (2019.02); *A61B 5/0816* (2013.01); *A61B 5/113* (2013.01); *A61B 5/1127* (2013.01); *A61B 6/022* (2013.01); *A61B 6/032* (2013.01); *A61B 6/12* (2013.01); *A61B 6/4014* (2013.01); *A61B 6/4085* (2013.01); *A61B 6/4266* (2013.01); *A61B 6/4464* (2013.01); *A61B 6/5223* (2013.01); *A61B 2034/107* (2016.02); *A61B 2034/2055* (2016.02); *A61B 2034/254* (2016.02); *A61B 2090/364* (2016.02); *A61B 2090/376* (2016.02); *A61B 2090/3945* (2016.02); *A61B 2090/3966* (2016.02); *A61N 5/1083* (2013.01); *A61N 2005/1051* (2013.01); *A61N 2005/1061* (2013.01); *A61N 2005/1062* (2013.01); *A61N 2005/1074* (2013.01); *G06T 2200/08* (2013.01); *G06T 2207/10124* (2013.01); *G06T 2207/20096* (2013.01); *G06T 2210/41* (2013.01); *G06T 2211/428* (2013.01)

(58) Field of Classification Search
CPC ...... A61B 2090/376; A61B 2090/3945; A61B 2090/3966; A61B 34/25; A61B 5/0816; A61B 5/1127; A61B 5/113; A61B 6/022; A61B 6/032; A61B 6/12; A61B 6/4014; A61B 6/4085; A61B 6/4266; A61B 6/4464; A61B 6/463; A61B 6/465; A61B 6/5223; A61B 6/5235; A61B 6/5288; A61B 6/5294; A61N 2005/1051; A61N 2005/1061; A61N 2005/1062; A61N 2005/1074; A61N 5/1037; A61N 5/1049; A61N 5/1067; A61N 5/1083; G06F 19/00; G06F 19/3418; G06T 11/008; G06T 17/00; G06T 19/00; G06T 19/20; G06T 2200/08; G06T 2207/10124; G06T 2207/20096; G06T 2210/41; G06T 2211/428; G06T 7/0016; G06T 7/20; G06T 7/251; G06T 7/38; G16H 30/40; G16H 40/63

See application file for complete search history.

(56) References Cited

U.S. PATENT DOCUMENTS

| | | |
|---|---|---|
| 2005/0180544 A1 | 8/2005 | Sauer |
| 2006/0291621 A1 | 12/2006 | Yan et al. |
| 2008/0212737 A1 | 9/2008 | D'Souza et al. |
| 2011/0249794 A1 | 10/2011 | Florent |
| 2012/0089015 A1 | 4/2012 | Gagnon |
| 2012/0109608 A1 | 5/2012 | Core et al. |
| 2013/0259338 A1 | 10/2013 | Brehm et al. |
| 2013/0266202 A1 | 10/2013 | Yamada |
| 2016/0302747 A1 | 10/2016 | Averbuch |

OTHER PUBLICATIONS

Fu et al., "Xsight Lung Tracking System: A Fiducial-Less Method for Respiratory Motion Tracking", Chpater 26, 265 pages, 2007, Section 6, Springer Berlin Heidelberg.
Ho et al., "A Study of the Accuracy of CyberKnife Spinal Radiosurgery Using Skeletal Structure Tracking", Operative Neurosurgery 1, Feb. 2007, 147 pages, vol. 60, Department of Radiation Oncology, Stanford University Medical Center, Stanford, CA, USA.
International Search Report and Written Opinion for PCT/US2017/013981 dated Apr. 3, 2017, 14 pages.
International Search Report and Written Opinion for PCT/US2017/013980 dated Apr. 18, 2017, 14 pages.
USPTO, Office Action for U.S. Appl. No. 15/005,971, dated Apr. 21, 2017.
Objections from the European Patent Office for European Patent No. 17703006.1 mailed Sep. 20, 2018, pp. 3.
Examination Report from the European Patent Office for European Patent No. 17703006.1, dated Jun. 25, 2020, pp. 7.
European Patent Convention Examination Report for European Application No. 17703006.1, dated Jun. 25, 2020, 7 pages.

| 440 | 450 | 460 | 430 |
|---|---|---|---|
| 1 | ~• | 0:15 | ✓ |
| 12 | ~• | 0:27 | ✓ |
| 13 | •~ | 0:19 | ✓ |
| 3 | ~• | 0:25 | X |
| 9 | ~• | 0:14 | ✓ |
| 5 | •~ | 0:28 | X |
| 10 | •~ | 0:12 | ✓ |
| 15 | ~• | 0:11 | ✓ |
| 7 | ~• | 0:10 | ✓ |

FIG. 4

PRESENTING A SEQUENCE OF IMAGES ASSOCIATED WITH A MOTION MODEL

CROSS-REFERENCE TO RELATED APPLICATIONS

This application is a continuation of U.S. patent application Ser. No. 15/005,985, filed Jan. 25, 2016, the contents of which are hereby incorporated by reference.

TECHNICAL FIELD

Aspects of the present disclosure relate to the presenting of images, and more specifically, relate to the presenting of a sequence of images associated with a motion model.

BACKGROUND

Reference images of a patient may be used to indicate the position of a target region of the patient during a radiation treatment procedure. For convenience, the term "radiation treatment" is used herein to mean radiosurgery and/or radiotherapy unless otherwise noted. Tracking of the treatment target increases the accuracy of the radiation treatment procedure so that irradiation of the healthy tissue surrounding the targeted region may be minimized.

A workflow to provide the radiation treatment to a patient may involve multiple stages corresponding to treatment planning, patient setup, and treatment delivery as described with regards to FIG. 1. As shown, the method 100 may begin with the treatment planning as a first stage to provide radiation treatment to the patient (block 110). The treatment planning stage may be initiated by obtaining of pre-treatment diagnostic images with one or more imaging modalities (e.g., CT image, MR image, etc.) of a volume of interest (VOI) of the patient. The treatment planning stage may further include identifying one or more reference points in one or more of the pre-treatment images. The reference points may be one or more imageable landmarks or points of interest in the acquired images that can be tracked during later stages discussed below. The acquired images in the treatment planning stage such as a CT image includes a pathological anatomy that is targeted for treatment, and well as a critical region(s) that is positioned near the pathological anatomy. Treatment planning software enables the generation of a critical region contour around the critical region and a target region contour around the pathological anatomy. Conventionally, a user manually delineates or uses a software tool to auto-delineate points on a display that is used by the treatment planning software to generate the corresponding contours. After the target has been defined, the critical and soft tissue volumes have been specified, and minimum radiation dose to the target and the maximum dose to normal and critical healthy tissue has been specified, the treatment planning software then produces a treatment plan, relying on the positional capabilities of the radiation treatment system.

The method 100 may subsequently include a patient setup as a second stage of the workflow before providing the radiation treatment to the patient (block 120). A stereo image may be generated, such as by X-ray imaging, or a 3D alignment image may be generated, such as a cone-beam CT (CBCT) or a megavoltage CT (MVCT) image, and then correlated to the preoperative image in order to locate the target region accurately. Then, a radiation source located on a treatment delivery system is automatically positioned based on the correlation between the preoperative image and the stereo images (or 3D alignment image) in order to accurately target the desired treatment region in the patient. If the patient is not within the desired range of the radiation treatment delivery system, the position of the patient adjusted during the patient setup stage.

After the patient setup stage, treatment delivery may be performed on the patient based on the treatment plan (block 130). The images(s) taken during the patient set up stage may be used as a delivery reference for later registration. During treatment delivery, dynamic tracking of the target may be performed based on the use of x-ray images taken to identify internal features in the patient and external markers to track motions of the target due to, for example, patient respiration, with the registration results between a digitally reconstructed radiograph (DRR) and each of the live x-ray images used to generate a correlation model. The external markers may be light emitting diodes (LEDs) that are coupled to the patient and a tracker or motion detection system to track the position of one or more of the external markers. An example of one such system is the Synchrony™ respiratory tracking system developed by Accuray, Inc. However, other respiratory tracking systems may be used. After the correlation model is generated, the position measurements of the external markers may be used to compute the corresponding location of the target by using the correlation model. Once the location of the target (e.g., the tumor) has been computed, the radiation beam source position of the radiation treatment delivery system may be adjusted to compensate for the dynamic motion of the target due to patient respiration (or other movement). The radiation treatment delivery system may then deliver the dose of radiation to the tracked target in accordance with the radiation treatment plan developed during the treatment planning stage.

Thus, a sequence of x-ray images of a patient may be acquired and a correspondence between a location of a tumor of the patient and the motion of the patient as represented by LED markers that are placed on the patient's body may be determined. After the model has been generated, the motion of the LED markers may be used to predict the location of the tumor. Such information may be used to dynamically update the delivery of the radiation treatment from the radiation treatment equipment to the patient so that the target is irradiated according to the treatment plan, even as the location of the target moves based on the motion of the patient.

The x-ray images may be obtained based on sequential acquisition of the x-ray images of the patient. Each x-ray image may be correlated with a DRR image as it is acquired and a determination may be made as to whether the correlation results of the x-ray image satisfy correlation criteria. If the x-ray image satisfies the correlation criteria, then the x-ray image may be used in the building of the correlation model. However, if the x-ray image doesn't satisfy the correlation criteria, then the correlation parameters of the x-ray image may be modified or the x-ray image may not be used in the building of the correlation model. Subsequently, another x-ray image may be acquired and the process may repeat. Thus, a user viewing the acquired x-ray images that are used to build the correlation model may only view or modify the most recently acquired x-ray image.

Furthermore, when viewing the most recently acquired x-ray image that has been used to build the correlation model, the visibility of a tumor within the x-ray image may be difficult when separately viewing the most recently acquired x-ray image. For example, to a user reviewing a single x-ray image, the boundaries, shape, and size of the tumor may be difficult to identify.

BRIEF DESCRIPTION OF THE DRAWINGS

The present disclosure will be understood more fully from the detailed description given below and from the accompanying drawings of various implementations of the disclosure.

FIG. 4 illustrates a table associated with a group of images in accordance with some embodiments.

DETAILED DESCRIPTION

Figure 1:
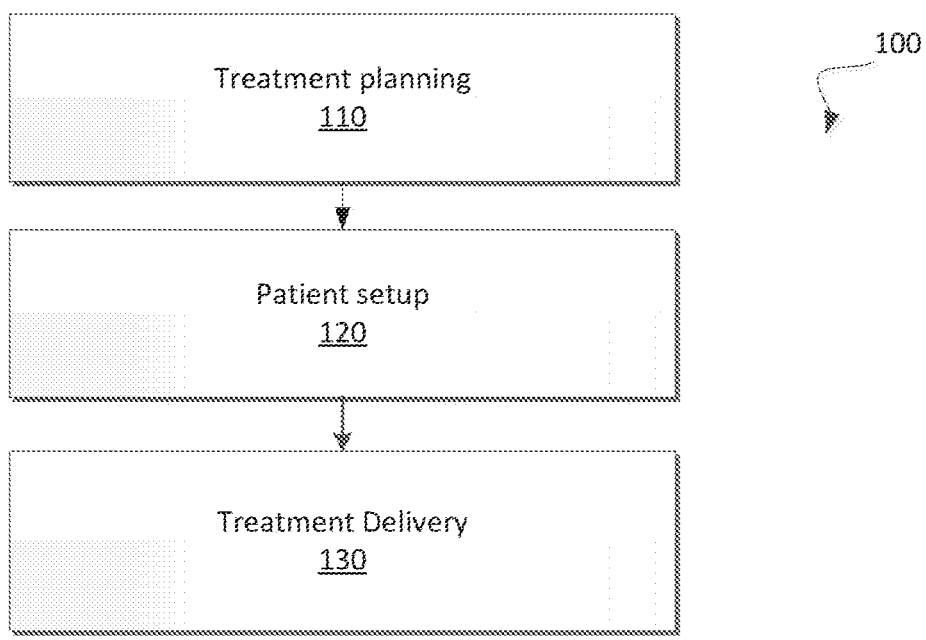
FIG. 1 is a flow diagram an example method to provide radiation treatment to a patient in accordance with some embodiments of the present disclosure.

Aspects of the present disclosure are directed to the presenting of a sequence of images associated with a motion model. In general, a radiation treatment procedure may target a region of a patient by providing radiation treatment focused to the targeted region. The model may be used to specify the targeted region during the operation of radiation treatment equipment that provides the radiation treatment to the targeted region.

The model used in the radiation treatment procedure may be based on a group of images of the patient. For example, the series of images may be based on pre-operative x-ray images of the patient. The x-ray images may include a region that is intended to be targeted by the radiation treatment (e.g., a tumor) and a region that is not intended to be targeted by the radiation treatment (e.g., surrounding healthy tissue). The model may be used to specify the targeted region for the radiation treatment provided by the radiation treatment equipment. In general, the model may be generated by a correlation process that identifies an object, such as the tumor, in the x-ray images. In one embodiment, the correlation process may be based on Xsight™ Lung, Xsight™ Spine, and Fiducial Tracking processes developed by Accuray, Inc. In alternative embodiments, other correlation processes may be used. The results of such a correlation process may be used to control the radiation treatment equipment. As such, the model may be generated using a series of x-ray images and may be used to control the providing of the radiation treatment to the targeted region of the patient. In some embodiments, a contour corresponding to the targeted region recognized by the correlation process may be superimposed upon the series of x-ray images to provide an indication of the targeted region on the x-ray images. Further details with regard to the contour are described below.

As such, the model may be based on a series of x-ray images. The x-ray images may be sequentially added to the model by the user creating the model. For example, the model may be based on a threshold or maximum number of images (e.g., fifteen x-ray images) and each x-ray image may be added to the model one at a time. For example, a first x-ray image may be provided to the user or viewer who may select to include the first x-ray image as one of the images in the model. After the user or viewer has provided a selection for the first x-ray image, then a second x-ray image may be provided to the user or viewer. If the user or viewer has selected to include fifteen x-ray images (e.g., the threshold or maximum number of images) in the model, but later decides to change the model by removing the seventh x-ray image of the fifteen x-ray images, then the user may begin to add additional x-ray images to be included in the model until the seventh x-ray image that the user intends to remove has been pushed out of the model. For example, the model may include fifteen x-ray images as a maximum number of x-ray images that may be included in the model. If the user seeks to remove the seventh x-ray image, then eight new x-ray images may be added to the model so that the seventh x-ray is pushed out of the model along with the eighth through fifteenth x-ray images and are replaced by other x-ray images.

Instead of removing the x-ray images that are used in the model by adding additional x-ray images to push out particular x-ray images, the x-ray images may be provided to the user or viewer as a group of images that may each be individually removed or added for use in the model. For example, instead of removing the seventh x-ray image in a series of images by adding new x-ray images to the model, the user or viewer may be provided a graphical user interface (GUI) that provides an option to remove or add any of the x-ray images for use in the model. In some embodiments, the GUI may provide a table that identifies each of the x-ray images that may be used in generation of the model. The table may identify, for each of the x-ray images, whether the x-ray image has already been included to be used in the generation of the model or whether the x-ray image has not been included to be used in the generation of the model, and other information related to each of the x-ray images. Furthermore, an entry of the table that corresponds to a particular x-ray image may be selected to provide a visual display of the x-ray image and a contour that is superimposed on the x-ray image where the contour represents where the radiation treatment will be provided (e.g., where the tumor is recognized by the correlation process relative to the x-ray image). As such, the GUI may provide the user or viewer to operate upon the x-ray images as a group or an ensemble as opposed to individual x-ray images in a sequential manner. Thus, the user or viewer may modify the model more easily by operating on parameters associated with each x-ray image in any order as opposed to being provided a sequential sequence of x-ray images.

The GUI may further provide or play the group of x-ray images that are included in the generation of the model in a sequence so that the tumor in the x-ray images may be more easily identifiable (i.e., a movie mode). For example, the x-ray images may be sorted based on a respiratory order of the patient. The playing or providing of the x-ray images that are sorted based on respiratory order in the movie mode may allow a user or viewer to more easily ascertain the location of the tumor around healthy tissue and bone structure during respiration of the patient. Furthermore, the contour that represents the targeted region for the radiation treatment may be superimposed on each x-ray image as the sorted x-ray images are played or provided to the user or viewer. Since the contour represents the targeted region of the radiation treatment, the user or viewer may verify that the contour contains the tumor in each x-ray image and may thus verify that the radiation treatment is targeting the correct region of the patient (e.g., the tumor and not healthy tissue) during the range of motion of respiration of the patient.

If the user or viewer identifies that the contour for at least one of the x-ray images is not encompassing the tumor from the x-ray image, then the user or viewer may modify or remove the x-ray image since the radiation treatment may not be correctly targeting the tumor based on the x-ray image. For example, as previously described, the user or viewer may use the GUI to remove the x-ray image from the group of images that are used to identify the targeted region (which may also be referred to as a tracking target). In some embodiments, the user or viewer may change parameters associated with the correlation process that is used to correlate the x-ray image with the targeted region. For example, correlation parameter thresholds may be adjusted so that x-ray images that were not previously considered successful may be considered successful based on the adjusted or new correlation parameter threshold. Furthermore, correlation parameter inputs may also be adjusted and the x-ray images may be re-correlated to produce successful results in response to the adjusted or new correlation parameter inputs. Although aspects of the present disclosure refer to a correlation process, other types of target location processes may be used. For example, other target location processes that may perform a computation of a similarity measure may be used. Such target location processes may include, but are not limited to, cross-correlation, normalized cross-correlation, pattern intensity, mutual information, normalized mutual information, mean squared difference, mean absolute difference, etc. Thus, embodiments of the present disclosure may alternatively use any type of target location process.

Accordingly, aspects of the present disclosure may allow a user or viewer to verify that the targeted region of the radiation treatment is correctly identified. If one of the x-ray images does not correctly target a tumor (e.g., the contour is not over the tumor and thus the correlation of the x-ray image is an error), then the user or viewer may use the GUI to either remove the x-ray image or to change parameters associated with the correlation process so that the targeted region of the radiation treatment contains the tumor instead of healthy tissue of the patient.

Figure 2:
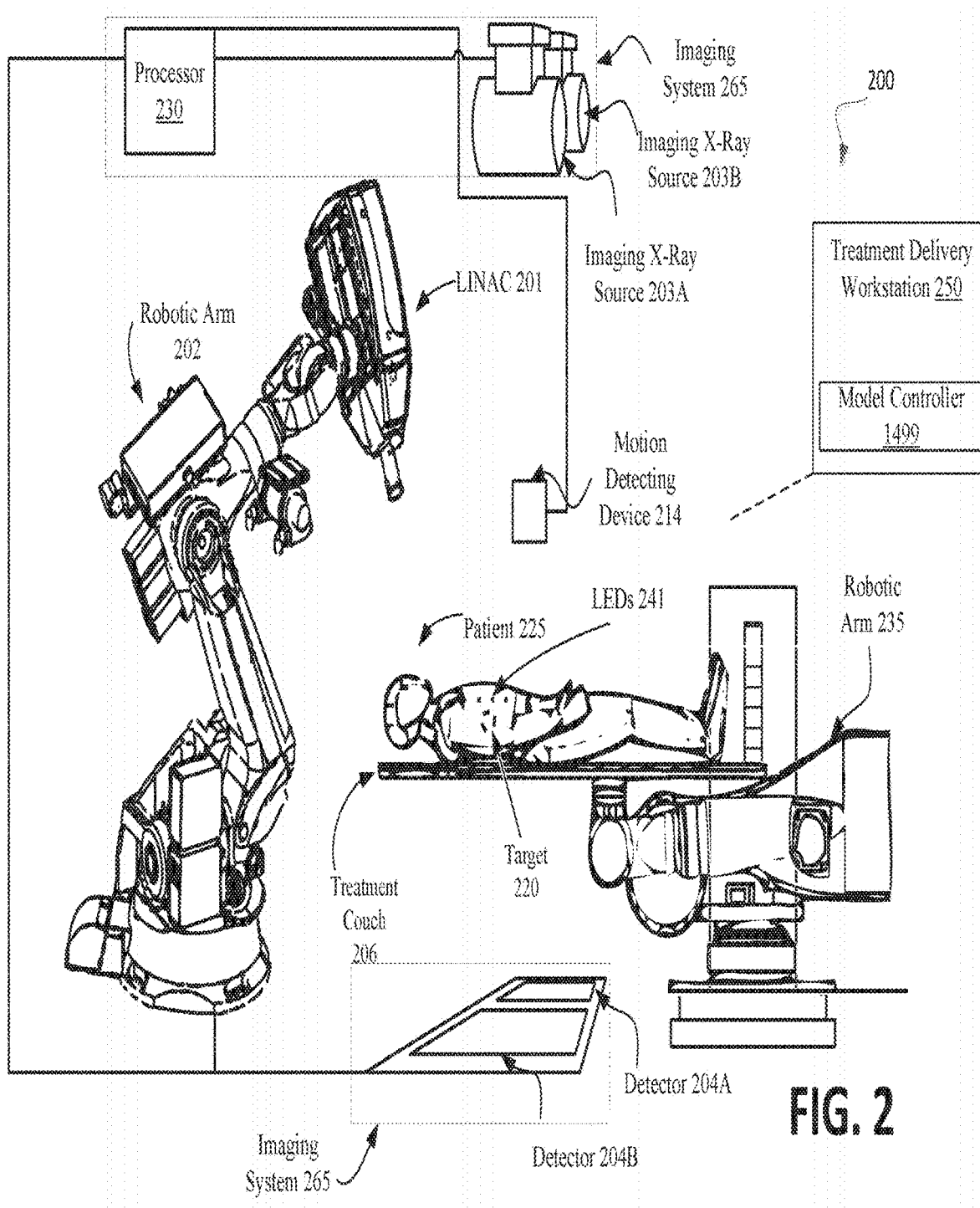
FIG. 2 illustrates an example of an image-guided radiation treatment system in accordance with some embodiments of the present disclosure.

FIG. 2 illustrates an example of an image-guided radiation treatment system 200. In general, the image-guided radiation treatment system 200 may provide radiation treatment to a targeted region of a patient based on a treatment plan from correlation results that are reviewed via the GUI 700 or 800 of FIG. 7 or 8.

As shown, FIG. 2 illustrates a configuration of an image-guided radiation treatment system 200. In the illustrated embodiments, the radiation treatment system 200 includes a linear accelerator (LINAC) 201 that acts as a radiation treatment source. In one embodiment, the LINAC 201 is mounted on the end of a robotic arm 202 having multiple (e.g., 5 or more) degrees of freedom in order to position the LINAC 201 to irradiate a pathological anatomy (e.g., target 220) with beams delivered from many angles, in many planes, in an operating volume around a patient. Treatment may involve beam paths with a single isocenter, multiple isocenters, or with a non-isocentric approach. Alternatively, other types of image guided radiation treatment (IGRT) systems may be used. In one alternative embodiment, the LINAC 201 may be mounted on a gantry based system to provide isocentric beam paths.

In one embodiment, the LINAC 201 may be positioned at multiple different nodes (predefined positions at which the LINAC 201 is stopped and radiation may be delivered) during treatment by moving the robotic arm 235. At the nodes, the LINAC 201 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated.

Referring to FIG. 2, the image-guided radiation treatment system 200 may include an imaging system 265 having a processor 230 connected with x-ray sources 203A and 203B and fixed x-ray detectors 204A and 204B. Alternatively, the x-ray sources 203A, 203B and/or x-ray detectors 204A, 204B may be mobile, in which case they may be repositioned to maintain alignment with the target 220, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 201 serves as an imaging source, where the LINAC power level is reduced to acceptable levels for imaging.

Imaging system 265 may perform computed tomography (CT) such as cone beam CT or helical megavoltage computed tomography (MVCT), and images generated by imaging system 265 may be two-dimensional (2D) or three-dimensional (3D). The two x-ray sources 203A and 203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 206 during treatment) and to illuminate imaging planes of respective detectors 204A and 204B after passing through the patient. In one embodiment, imaging system 265 provides stereoscopic imaging of the target 220 and the surrounding volume of interest (VOI). In other embodiments, imaging system 265 may include more or less than two x-ray sources and more or less than two detectors, and any of the detectors may be movable rather than fixed. In yet other embodiments, the positions of the x-ray sources and the detectors may be interchanged. Detectors 204A and 204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

The image-guided radiation treatment 200 may include a motion detection device 214 to determine target motion within a detection field. The motion detecting device 214 may detect external patient motion (such as chest movement during respiration) that occurs within an area of the patient 225. The motion detecting device 214 can be any sensor or other device capable of identifying target movement. The motion detecting device 214 may be an optical sensor such as a camera, a pressure sensor, an electromagnetic sensor, or some other sensor that may provide motion detection without delivering ionizing radiation to a user (e.g., a sensor other than an x-ray imaging system). In one embodiment, the motion detecting device 214 acquires measurement data indicative of target motion in real-time. Alternatively, the measurement data may be acquired at a frequency that is higher (than can be achieved or than is desirable with x-ray imaging (due to ionizing radiation delivered to the patient with each x-ray image). In one embodiment, the motion detecting device 214 does not provide high absolute position accuracy. Instead, the motion detecting device 214 may provide sufficient relative position accuracy to detect patient movement and/or target movement.

In one embodiment, the motion detecting device 214 is an optical system, such as a camera. The optical system may track the position of light-emitting diodes (LEDs) 241 situated on patient 225. Alternatively, the optical system may directly track a surface region of patient 225, as distinguished from tracking LEDs 241 on the patient. There may be a correlation between movement of the target and movement of the LEDs 241 and/or surface region of the patient 225. Based on the correlation, when motion of the LEDs 241 and/or surface region is detected, it can be determined that the target 220 has also moved sufficiently to require another diagnostic x-ray image to precisely determine the location of the target.

As shown in FIG. 2, the image-guided radiation treatment system 200 may further be associated with a treatment delivery workstation 250. The treatment delivery workstation may be remotely located from the image-guided radiation treatment system 200 in a different room that the treatment room in which the system 200 and patient are located. The treatment delivery workstation 250 may include a processing device and memory that implements a model controller 1499 that provides a first GUI (e.g., GUI 700 of FIG. 7) and a second GUI (e.g., GUI 800 of FIG. 8) to display the x-ray images acquired by the imaging system 265. The first GUI may identify the x-ray images that are used to identify the target 220 based on a respiratory order of the patient 225 and the second GUI may identify images acquired by the imaging system 265 that are both used to identify the target 220 and that are not used to identify the target 220.

In some embodiments, a gantry system with a helical delivery may be used to rotate the imaging system 265. For example, the gantry system may be used to acquire two, three, or more images (e.g., x-ray images) at different angles that may be provided to a user in a GUI as described in further detail in conjunction with FIG. 7.

Figure 3:
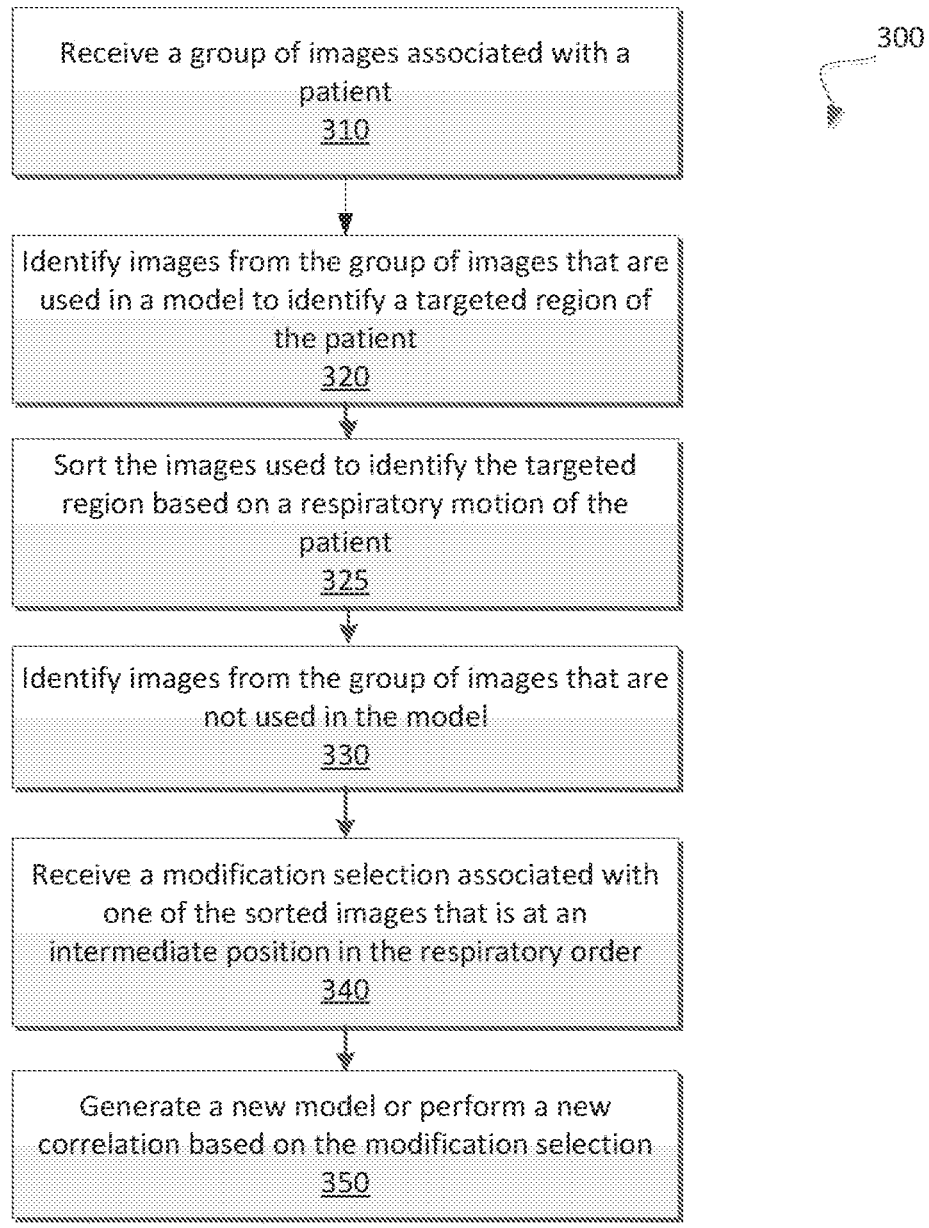
FIG. 3 is a flow diagram of an example method to use a model based on a selection of an image in a group of images in accordance with some embodiments of the present disclosure.

FIG. 3 is a flow diagram an example method to generate a model based on a selection of an image in a group of images. In general, the method 300 may be performed by processing logic that may comprise hardware (e.g., processing device, circuitry, dedicated logic, programmable logic, microcode, hardware of a device, integrated circuit, etc.), software (e.g., instructions run or executed on a processing device), or a combination thereof. In some embodiments, the method 300 is provided via the graphical user interface (GUI) 700 or 800 of FIGS. 7 and 8.

As shown in FIG. 3, the method 300 may begin with the processing logic receiving a group of images associated with a patient (block 310). For example, images of a first modality representing a patient may be received. In some embodiments, the images may correspond to x-ray images of a region of a patient. In the same or alternative embodiments, pairs of x-ray images of the region of the patient may be received. The processing logic may further identify images of the group of images that are used in a model that is used to target a region of the patient (block 320). For example, each of the identified x-ray images may be used to identify the targeted region of the patient that will receive a radiation treatment for the targeted region. In some embodiments, the images that are used in the generation of the model may be x-ray images that satisfy correlation parameter thresholds. The processing logic may subsequently sort the images that are used to identify the targeted region based on a respiratory motion of the patient (block 325). For example, each of the x-ray images may be sorted based on a position within the respiratory motion of the patient. A first position in the respiratory motion may correspond to the beginning point of the respiratory motion of the patient and a last position in the respiratory motion may correspond to the final point of the respiratory motion of the patient. An intermediate position may correspond to a middle point that is between the beginning point and the final point of the respiratory motion of the patient. Further details with regard to sorting images based on respiratory motion are described in conjunction with FIG. 10.

Referring to FIG. 3, the processing logic may further identify images from the group of images that are not used in the generation of the model that is used to target the region of the patient (block 330). For example, x-ray images that do not satisfy the correlation parameter thresholds may be identified. The processing logic may further receive a modification selection associated with one of the sorted images that is at an intermediate position in the respiratory order (block 340). The modification selection may correspond to a removal of one of the images or a modification of a parameter associated with one of the images that are used in the generation of the model. For example, the selection may remove an x-ray image that is at the intermediate position and is currently used in the generation of the model or may correspond to a changing of a correlation parameter threshold that may be used to indicate whether or not an x-ray image is successfully or not successfully correlated. The modification selection may further be a change to a correlation parameter input where a change in the correlation parameter input may result in a re-correlation of images as described in further detail below. A GUI that may be used to provide the modification selection associated with the group of images as described with regard to FIGS. 7 and 8. The processing logic may further generate a new model or may perform a new correlation process based on the modification selection (block 350). For example, a new model may be generated based on a removing of an x-ray image at an intermediate position and that was used in the generating of the previous model, a changing of a correlation parameter threshold associated with the group of images that may identify which of the x-ray images in the group of images satisfy the changed correlation parameter threshold and which of the x-ray images do not satisfy the changed correlation parameter threshold, or a changing of a correlation parameter input which may perform a re-correlation of the x-ray images.

Furthermore, in some embodiments, the modification selection may correspond to including an x-ray image to be used in the generation of the model when the x-ray image was not previously used in the generation of the model. Thus, a new model may further be generated based on the adding of an x-ray image that was previously identified as not being used in the model. The added x-ray may further be at an intermediate position relative to the respiratory order or motion of the patient.

As such, a user may be provided with a GUI that provides an indication of each of the images that are used in the generation of a model to provide radiation treatment to a targeted region of a patient as well as an indication of each of the images that are not used in the generation of the model. A selection may be made via the GUI of one of the images to modify the image or to change correlation parameter thresholds or correlation parameter inputs associated with the correlation process that has analyzed the group of images. The modification may be to add, remove, or modify parameters. associated with the model.

FIG. 4 illustrates a table 400 associated with a group of images. In general, the group of images may be associated with a model that is used to provide radiation treatment to a targeted region of a patient. The table 400 may be provided in a GUI 800 as described in conjunction with FIG. 8.

As shown in FIG. 4, the table 400 may include multiple entries or rows where each row or entry may correspond to an image (e.g., an x-ray image) in an image history of a patient. For example, a first row or entry 410 may correspond to a first x-ray image and a second row or entry 420 may correspond to a second x-ray image. In some embodiments, the table 400 may identify whether an x-ray image is currently being used in a model to identify a target region of a patient or whether the x-ray image is not being used in the model to identify the target region. For example, the table 400 may include a column 430 that identifies whether a corresponding image is currently being used by the model (e.g., represented by a checkmark) and whether the corresponding image is not currently being used in the model (e.g., represented by an 'X'). As shown, the row or entry 410 may identify that the first image is being used in the model and the row or entry 420 may identify that the second image is not currently being used in the model.

Furthermore, a column 440 may identify a model point associated with each of the x-ray images. Furthermore, a column 450 may identify a phase of each corresponding x-ray image relative to a respiratory order associated with the patient. For example, the column 450 may identify a position of the corresponding x-ray image after the images have been sorted based on respiratory order of the patient. The position may be illustrated by a marker (e.g., a circle or a dot) that identifies the point in the respiratory phase (e.g., a peak, a valley, rising middle, falling middle, etc.) of the patient when the x-ray image was acquired. Further details with regard to sorting of the x-ray images based on respiratory order are described in conjunction with FIG. 10. Furthermore, the table 400 may include a column 460 that may identify a time associated with the age of each corresponding x-ray image. For example, the table 400 may identify images of a patient that were taken during a particular time period (e.g., thirty seconds) and may identify the age of each of the images relative to the current time. In some embodiments, the times identified in the column 460 may be dynamic and updated as time progresses. Furthermore, the table 400 may be sorted based on any of the columns 430, 440, 450, and 460. For example, the rows of the table 400 may be provided in a first order based on a selection of the column 460 (e.g., based on ascending or descending order of the age of each image) or a second order based on a selection of the column 430 so that images included in the model are provided in the table above or below the images that are not included in the model.

As such, the table 400 may indicate whether each x-ray image is used or is not used in the identification of a targeted region of a patient as well as additional information associated with each of the images. Further details with regard to a GUI that may be provided to a user or a viewer with regard to x-ray images used to generate the model are described in conjunction with FIGS. 7 and 8.

Figure 5:
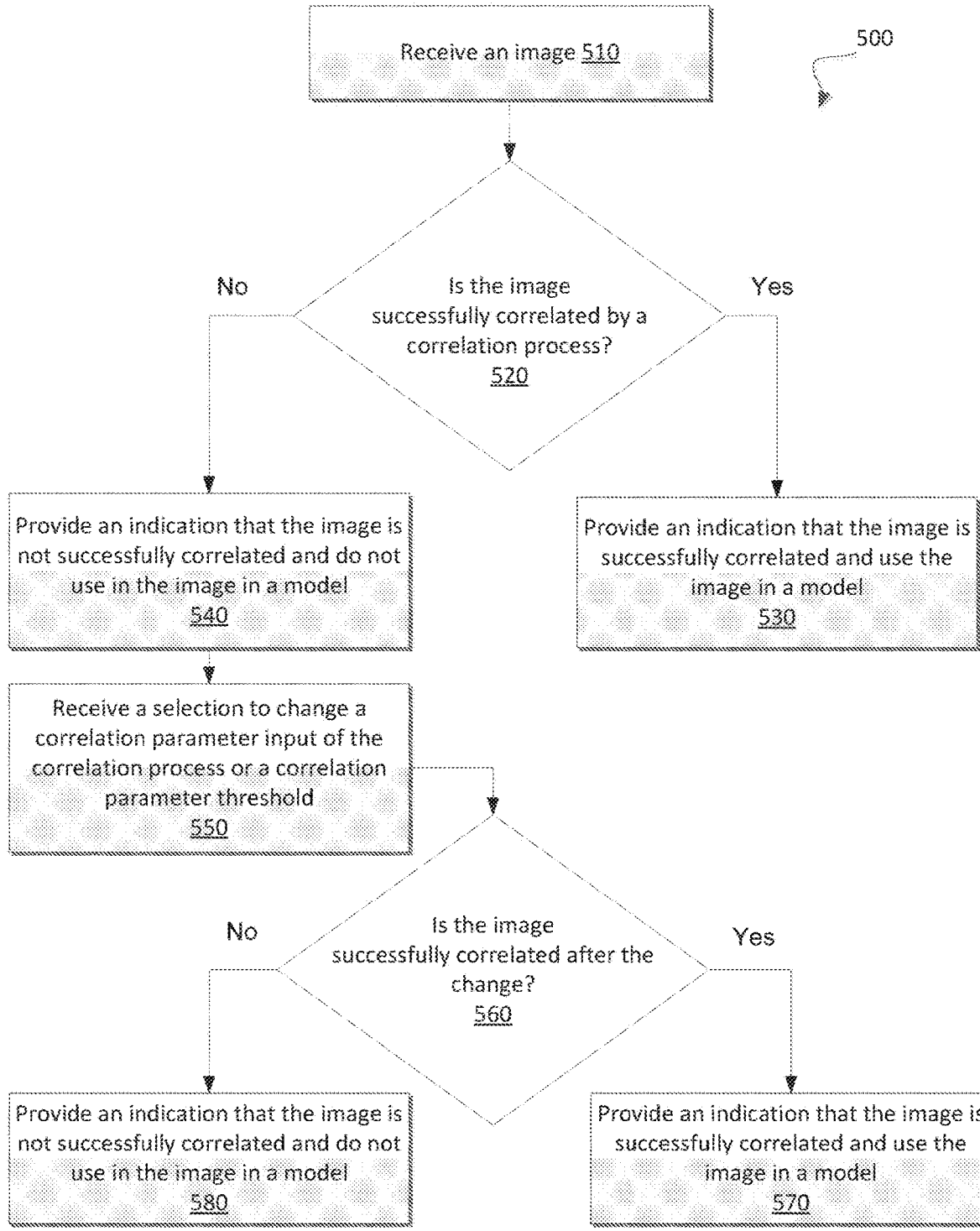
FIG. 5 is a flow diagram of an example method to include an image that was not successfully correlated in a group of images to be used in a model in accordance with some embodiments of the present disclosure.

FIG. 5 is a flow diagram of an example method 500 to include an image that was not successfully correlated in a group of images to generate a model. In general, the method 500 may be performed by processing logic that may comprise hardware (e.g., processing device, circuitry, dedicated logic, programmable logic, microcode, hardware of a device, integrated circuit, etc.), software (e.g., instructions run or executed on a processing device), or a combination thereof. In some embodiments, the method 500 is provided via the graphical user interface 700 or 800 of FIGS. 7 and 8.

As shown in FIG. 5, the method 500 may begin with the processing logic receiving an image (block 510). For example, an x-ray image of a patient may be received. The processing logic may determine whether the image has been successfully correlated (block 520). For example, a determination may be made as to whether one or more correlation parameters that is provided by a correlation (or image registration or target localization) process of the x-ray image satisfy correlation parameter thresholds. If the image was successfully correlated (e.g., the correlation parameters satisfy the correlation parameter thresholds), then the x-ray image may be used to generate the model (block 530). Furthermore, a GUI may provide an indication or identify that the image has been used to generate the model for identifying a targeted region of the patient and/or has been successfully correlated. However, if the x-ray image was not successfully correlated (e.g., the correlation parameters for the x-ray image do not satisfy the correlation parameter thresholds), then the processing logic may not use the x-ray image to generate the model (block 540). For example, the x-ray image may not be used in the identification of a targeted region of the patient and the GUI may provide an indication or identify that the image has not been used to generate the model and/or was not successfully correlated. In some embodiments, an image may not be successfully correlated when the correlation process fails to localize the targeted region (e.g., a confidence metric or parameter is low or does not satisfy a threshold value) or by an input provided by a user. Furthermore, the processing logic may receive a selection to change a correlation parameter input or a correlation parameter threshold (block 550). Subsequently, the processing logic may determine if the image is now successfully correlated after the change to the correlation parameter input or the correlation parameter threshold (block 560). In response to determining that the image is now successfully correlated, the processing logic may provide an indication that the image is now successfully correlated and use image in the model (block 570) or in response to determining that the image is still not successfully correlated, the processing logic may provide an indication that the image is still not successfully correlated and may not use the image in the model (block 580). For example, the correlation parameter thresholds for the correlation process that is used to correlate the group of x-ray images may be changed and the x-ray image that was previously not successfully correlated may be considered to be successfully correlated if the correlation parameters of the image satisfy the updated correlation parameter thresholds. Subsequently, a new model based on the x-ray image that was not included in the previous model may be generated or used by the model to identify the targeted region.

Figure 6A:
FIG. 6A illustrates an example of a group of images that are used in a model in accordance with some embodiments.

FIG. 6A illustrates an example of a group of images 600 that are used to generate a model. As shown in FIG. 6A, the group of images 600 may include a first x-ray image 610, a second x-ray image 620, third x-ray image 630, fourth x-ray image 640, and a fifth x-ray image 650. In some embodiments, each image may correspond to an x-ray image. At a first time, the first x-ray image 610, third x-ray image 630, and fourth x-ray image 640 may be used in the generation of a model that is used to identify a targeted region for receiving radiation treatment. For example, the first, third, and fourth x-ray images 610, 630, and 640 may be associated with correlation parameters that satisfy correlation parameter thresholds. As such, the first x-ray image 610, third x-ray image 630, and fourth x-ray image 640 may be selected to be used in the generation of a model 660. However, the second x-ray image 620 and fifth x-ray image 650 may not be associated with correlation parameters that satisfy correlation parameter thresholds. As such, the second x-ray image 620 and the fifth x-ray image 650 may not be selected to be used in the generation of the model 660.

Figure 6B:
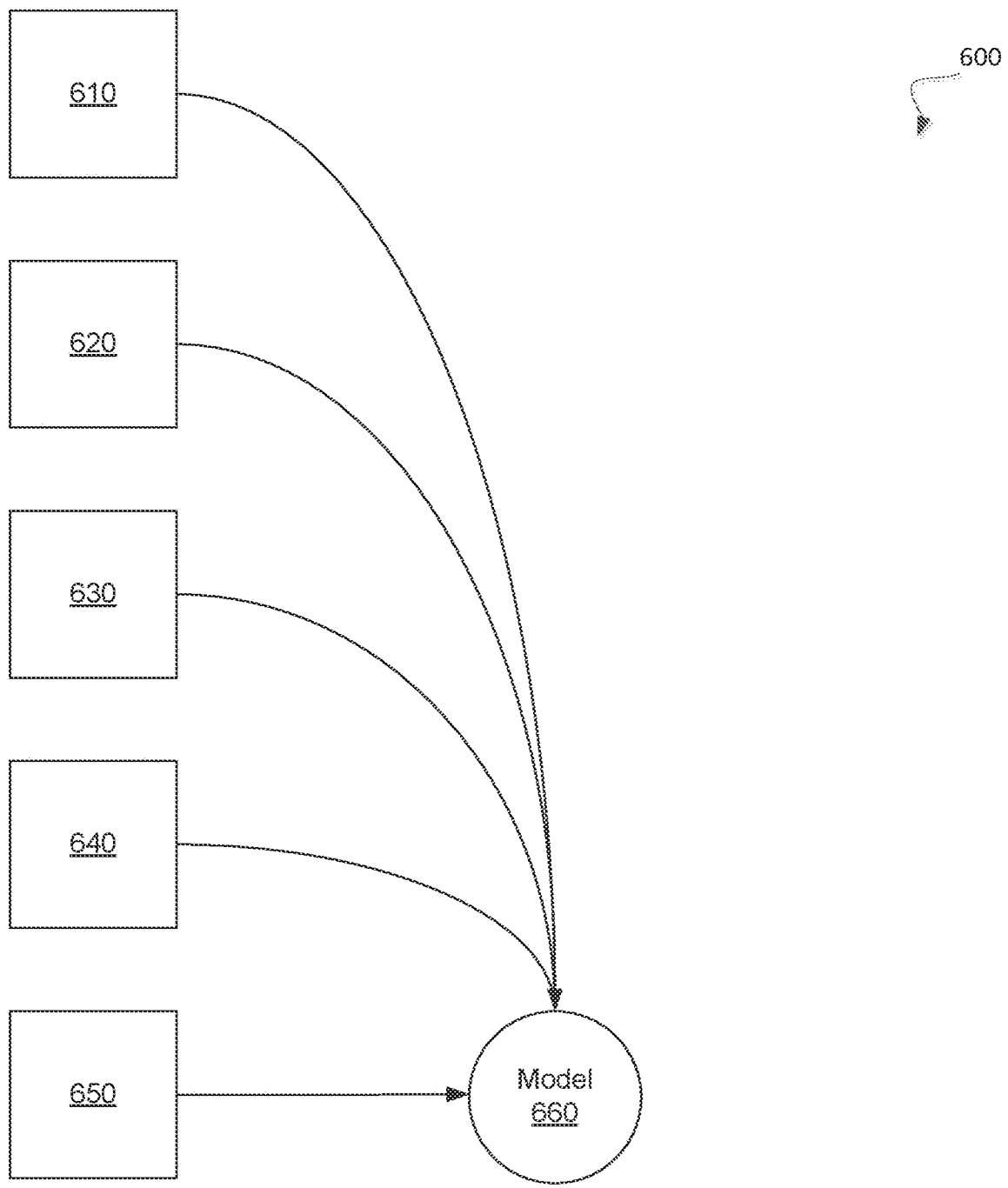
FIG. 6B illustrates an example of the group of images with a modification in accordance with some embodiments of the present disclosure.

FIG. 6B illustrates an example of the group of images 600 with a modification. In general, at a second time that is after the first time when the first x-ray image 610, third x-ray image 630, and fourth x-ray image 640 satisfied the correlation parameter thresholds and were used in the generation of the model, additional images may be used in the generation of a subsequent model. For example, a user may use a graphical user interface, as described in further detail with regard to FIGS. 7 and 8, to modify correlation parameter thresholds for the group of images 600. In response to the modifying of the correlation parameter thresholds, a determination may be made as to whether the correlation parameters for each of the x-ray images 610, 620, 630, 640, and 650 satisfy the new correlation parameter thresholds. For example, the modification to the correlation parameter thresholds may decrease requirements for a correlation parameter of a particular x-ray image. As such, while the correlation parameters associated with the second x-ray image 620 and fifth x-ray image 650 did not satisfy the previous correlation parameter thresholds, the correlation parameters of the second and fifth images 620 and 650 may satisfy the correlation parameter thresholds after being modified by the user to decrease the requirements of the correlation parameter thresholds. As such, a user may subsequently select the second x-ray image 620 and the fifth x-ray image 650 to be included in the generation of a new model 670.

As such, at a first time, a determination may be made as to whether each image of a group of images is associated with one or more correlation parameters that satisfy one or more correlation parameter thresholds. If the images satisfy the one or more correlation parameter thresholds, then an indication may be provided that the respective images are successfully correlated and the images may be selected to be used in a model. At a second time, updated correlation parameter thresholds may be provided and a second determination may be made as to whether each image in the group of images is associated with one or more correlation parameters that satisfy one or more updated correlation parameter thresholds. Additional images or fewer images may subsequently be identified as being associated with correlation parameters that satisfy the updated correlation parameter thresholds at the second time. Thus, the selection of images that are used to generate the model may be changed or modified based on the updated correlation parameter thresholds.

Figure 7:
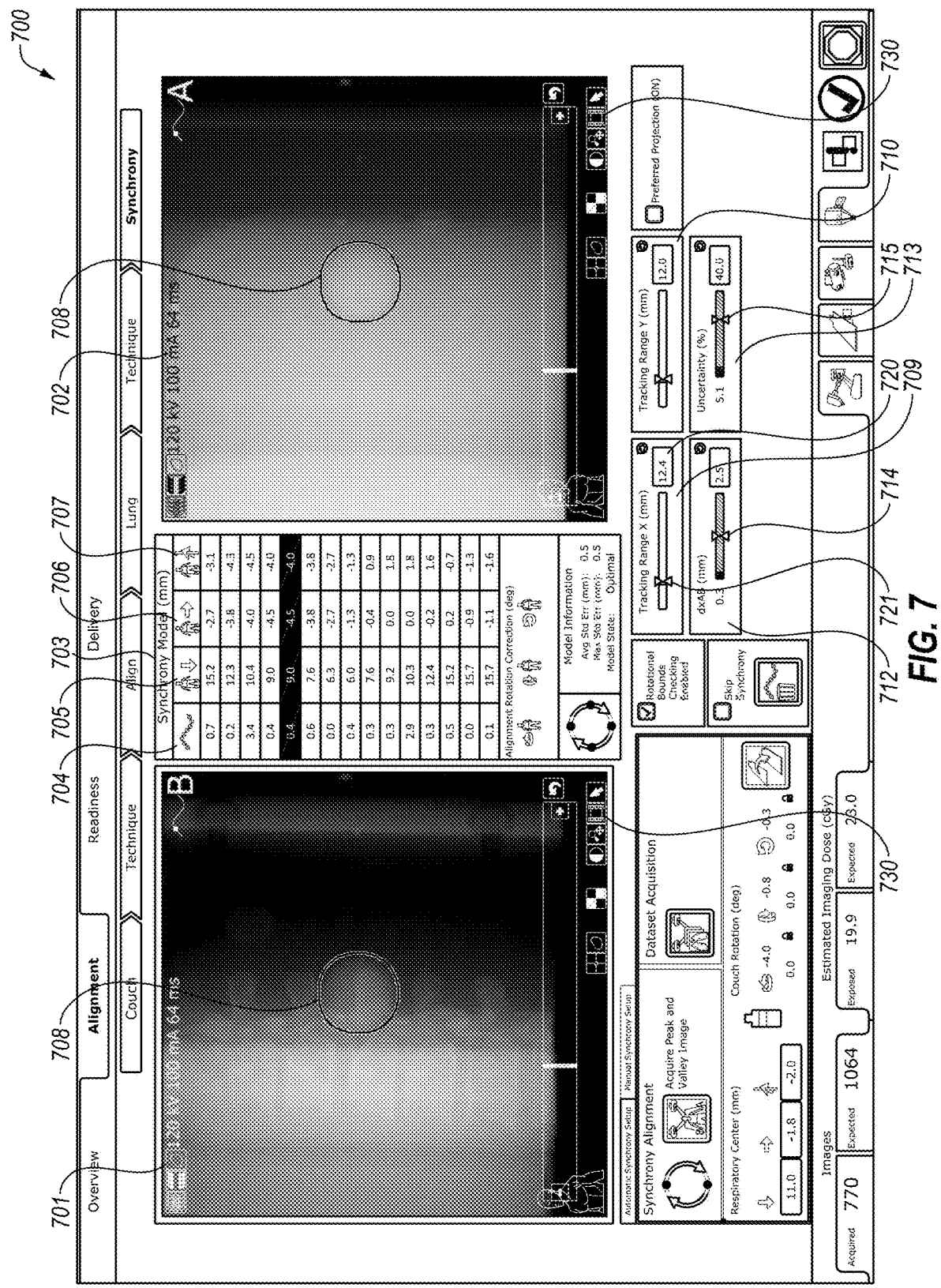
FIG. 7 illustrates a portion of an example graphical user interface in accordance with some embodiments of the present disclosure.

FIG. 7 illustrates a portion of an example graphical user interface (GUI) 700. In general, the GUI 700 may be used to modify a selection of a group of images used to generate a model to provide radiation treatment to a targeted region of a patient as described with regard to FIGS. 1 and 2. The GUI 700 may refer to the targeted region corresponding to a lung tumor, but the GUI 700 may be used with identifying target regions based on fiducial markers and spine tumors.

As shown in FIG. 7, the GUI 700 may include a pair of x-ray images that includes a first x-ray image 701 and a second x-ray image 702. In some embodiments, the first x-ray image 701 and the second x-ray image 702 may correspond to x-ray images of the patient from two different angles. For example, the first x-ray image 701 may be taken from a first angle (e.g., a forty five degree angle) and the second image 702 may be taken from a second angle (e.g., a one hundred thirty five degree angle). Each of the x-ray images 701 and 702 may include an identified tumor of the patient. Thus, each of the first and second x-ray images 701 and 702 may represent images of a tumor and surrounding healthy tissue and bone structure of the patient from different sides. Furthermore, each of the first x-ray image 701 and the second x-ray image 702 may include a contour 708 that represents the targeted region of the patient as identified by the correlation process as previously described. In some embodiments, if fiducial marker tracking is implemented, then fiducial marker graphics may be superimposed on each of the x-ray images instead of the contours. The fiducial marker may indicate a location for which a fiducial may have been identified.

The GUI 700 may further include a table 703 that corresponds to candidate images that may be included in the model that is used to identify the targeted region of the patient. The table 703 may identify each x-ray image from multiple x-ray images that are available to be selected to be used by the model to identify the targeted region. In some embodiments, the table 703 may include a column 704 that identifies an amount of error for each corresponding x-ray image. The error may be based on a 3D distance (e.g., in millimeters) of a point of the x-ray image from a fitted motion model. For example, if the fitted motion model is a linear model, the error may be based on the distance between the location of an object (e.g., a tumor) as identified on the pair of x-ray images and the nearest point on the linear motion model. If the object moves across a straight line, then the error may be at a value of '0.' However, if the object does not move across a straight line, then the error may be at a value that is larger than '0.' Furthermore, the column 705 may indicate an offset in a particular axis (e.g., an x-axis), the column 706 may indicate another offset in another axis (e.g., the y-axis), and the column 707 may indicate another offset in a third axis (e.g., the z-axis). Each of the columns 706-708 may indicate a distance of the tumor that is identified in the x-ray image with respect to the location of the tumor image in the DRR. For example, for a particular pair of x-ray images, the column 705 may indicate how far the identified tumor is relative to the tumor image in the DRR relative to the x-axis of each of the pair of x-ray images. Thus, the table 703 may indicate an error and offsets for each pair of x-ray images that is selected to be used in the model to identify a targeted region of a patient.

The GUI 700 may further include correlation parameter inputs corresponding to a first tracking range selection 709 and a second tracking range selection 710. Each of the first tracking range selection 709 and the second tracking range selection 710 may specify a distance in each axis that may be searched in the x-ray images to identify the targeted region. In general, if a tracking range is too small, then the targeted region (e.g., the tumor) may not be detected once the tumor leaves the tracking range and if the tracking range is too large, then computation times may be excessive and other objects may be erroneously identified as a match for the targeted region. As such, the first tracking range selection 709 may correspond to a tracking range in an x-axis for a correlation process that identifies the targeted region of a patient from the x-ray image and the second tracking range selection 710 may correspond to a tracking range in a y-axis for the correlation process that identifies the targeted region of the patient. The first and second tracking range selections 709 and 710 may be inputs or parameters to be used by the correlation process (i.e., correlation parameter inputs). For example, a user of the GUI 700 may provide or select a new value for one or both of the first tracking range selection 709 and the second tracking range selection 710 and the correlation process for each of the x-ray images of the model (e.g., as represented in the table 703) may be recomputed (i.e., the x-ray images are re-correlated) to determine whether each of the x-ray images currently used in the model are associated with new correlation parameters results that satisfy correlation parameter thresholds after the re-correlating of the x-ray images. For example, the first correlation parameter threshold for the result 'dxAB' may indicate, for each of the x-ray images, whether the corresponding correlation parameter result 712 satisfies a respective correlation parameter threshold 714 for dxAB and the second correlation parameter threshold 713 may indicate whether the second correlation parameter result 713 for Uncertainty Percentage associated with the x-ray image satisfies another correlation parameter threshold 715. In some embodiments, the first correlation parameter result 'dxAB' may be a detection quality metric that may be used to indicate an inconsistent result. For example, as previously mentioned, pairs of x-ray images of the patient may be acquired. If the object, or tumor, is identified in both of the x-ray images, then the position of the tumor along the x-axis may be equal in each of the x-ray images. The first correlation parameter result for 'dxAB' may provide a value corresponding to any difference of the position of the tumor along the x-axis of the pair of x-ray images. A large difference in distance may indicate a failed detection. Furthermore, the second correlation parameter result 713 may correspond to a detection confidence metric. In some embodiments, the detection confidence metric may be based on a number of local maxima near a global maximum, convexity of the objective function, etc.

As an example, a user of the GUI 700 may change or modify the correlation parameter inputs to the correlation process by providing a new value for the first tracking range selection 709 and a new value for the second tracking range selection 710. In some embodiments, the new value may be provided by entering the new value in a text box (e.g., a text box 720) or by using a slider 721 so that moving the slider to the left may decrease the new value and moving the slider to the right may increase the new value. In response to the entering of the new value or new values, the correlation process may be performed on the x-ray images of the table 703 to re-correlate the x-ray images. New correlation parameter results may be determined and a determination may be performed as to which of the x-ray images associated with the new correlation parameter results satisfies correlation parameter thresholds. For example, a first correlation parameter result 712 and a second correlation parameter result 713 may be provided for each of the x-ray images as well as an indication as to whether the correlation parameter results for each corresponding image satisfies the correlation parameter thresholds 714 and 715. For example, the first correlation parameter result 712 for 'dxAB' and the second correlation parameter result 713 may be re-calculated for each x-ray image in response to the re-correlation of the x-ray images. If the value of the first correlation parameter result 712 exceeds a correlation parameter threshold 714, then the first correlation parameter result 712 of the particular x-ray image may not be considered to satisfy the correlation parameter threshold 714. However, if the value of the first correlation parameter result 712 does not exceed the correlation parameter threshold 714, then the first correlation parameter result 712 of the x-ray image may be considered to satisfy the correlation parameter threshold 714. Similarly, if the second correlation parameter result 713 does not exceed the correlation parameter threshold 715, then the second correlation parameter result 714 for the x-ray image may be considered to satisfy the correlation parameter 715.

In some embodiments, a selection of one of the rows from table 703 may provide the x-ray images corresponding to the row to be displayed (e.g., at locations of x-rays 701 and 702) and to provide the correlation information of the x-ray images associated with the row (e.g., the correlation parameters and correlation parameter thresholds).

As such, a group of images may be provided via the GUI where each of the images may be a candidate image to be included in the model. Correlation parameter inputs that are used by a correlation process may be changed to re-correlate each of the images and the correlation parameter results may be determined by the correlation process with the new inputs. An indication may be provided as to whether each of the images with the new correlation parameter results satisfies the correlation parameter thresholds. Furthermore, correlation parameter thresholds may be changed and a new determination may be made as to whether current correlation parameter results of each of the images satisfies the new correlation parameter thresholds. Images that satisfy the correlation parameter thresholds may be successful candidates to be included in the model while images that do not satisfy the correlation parameters may not be successful candidates to be included in the model.

Figure 8:
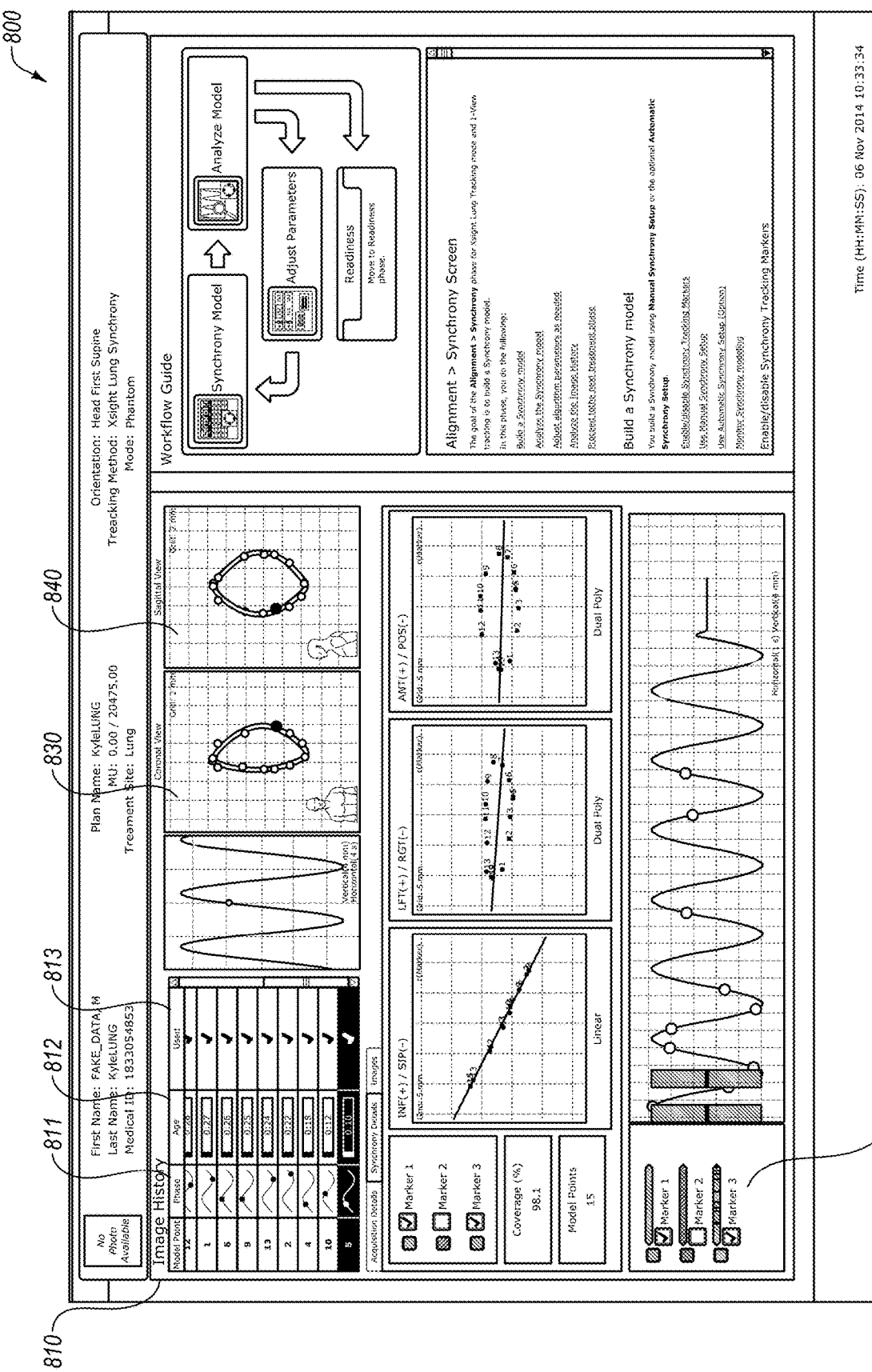
FIG. 8 illustrates another portion of an example graphical user interface in accordance with some embodiments of the present disclosure.

FIG. 8 illustrates another portion of an example graphical user interface 800. In general, the GUI 800 may be used to provide additional information to modify the selection of a group of images as described in conjunction with FIG. 7. In some embodiments, the GUI 800 may be provided with the GUI 700 of FIG. 7. For example, the GUI 700 and the GUI 800 may be simultaneously displayed or provided to a user or viewer.

As shown in FIG. 8, the GUI 800 may include a table 810 that includes multiple x-ray images, or pairs of x-ray images, of the patient. Furthermore, the table 810 may be referred to as an image history of the patient over a particular time period. For example, the table 810 may include multiple images acquired of a patient and one or more of the images in the table 810 may be selected to be included as a candidate image for the model to be provided in the table 703. The table 810 may include a column 811 that identifies, for each of the x-ray images, a position of the x-ray image in a sorted respiratory order of the patient. Further details with regard to the sorting based on respiratory order are described in conjunction with FIG. 10. The column 812 may identify the age of each of the x-ray images. For example, the x-ray images in the table 811 may be all x-ray images that were taken of a patient over a particular time period. The age of each image may be relative to the current point in time and the age may be updated as time progresses. Furthermore, the column 813 may indicate whether each of the x-ray images in the table 811 have been selected to be used or have not been selected to be used in the model to identify the targeted region of the patient. For example, if an x-ray image (or a pair of x-ray images) is selected to be included as a candidate image in the use of the model to identify the targeted region of the patient (e.g., in response to a selection in the column 813), then the x-ray image (or pair of x-ray images) may also be identified in the table 703 of the GUI 700. In some embodiments, the table 810 or image history of the patient may include more x-ray images than the table 703 of the x-ray images that have been selected for use as candidate images in the model. Thus, a selection to remove one of the x-ray images from the model may be provided by an input on the selection icon of column 813. Furthermore, the table 810 may be sorted based on a value corresponding to a selection of the columns 811, 812, and 813. As such, the table 810 may include a subset of the x-ray images from the table 703. For example, the table 810 may include a proper subset of the x-ray images from the table 703 (e.g., less x-ray images than the table 703) or may identify every image from the table 703.

Thus, the GUI 800 may include a table corresponding to an image history of the patient. Images from the image history may be selected to be included as candidate images for the model that is used to identify the targeted region of the patient as well as images that were previously included in the model may be removed from the model so that the image is no longer used in the identifying of the targeted region.

Referring to FIG. 8, the GUI 800 may further include a portion 820 that may indicate a position of the patient as represented by the selected x-ray image relative to one or more markers. For example, a marker (e.g., an LED marker) may be selected or removed from being used in the indication of the position of the portion of the patient relative to the selected x-ray image. The markers may be used to identify a location of the x-ray image relative to a respiratory order of the patient. The GUI 800 may further include a coronal view graph 830 and a sagittal view graph 840 of the x-ray images that are used in the model. For example, the coronal view graph 830 and the sagittal view graph 840 may provide a display of a correlation result in a particular plane (e.g., the coronal plane or the sagittal plane of a patient). Each of the coronal view graph 830 and the sagittal view graph 840 may display a path associated with the targeted region identified by the model and may illustrate a point on the path for each x-ray image that is included in the model. In some embodiments, a deviation from an expected path may indicate that a correlation using a particular x-ray image may be invalid or incorrect (e.g., an error associated with the correlation process when analyzing the x-ray image) and a user of the GUI 800 may select a portion of the path or a graphical indicator (e.g., a dot or circle) that is invalid or incorrect and may receive a selection of the corresponding x-ray image in the table 703 and table 810. The user may subsequently provide a selection in the table 811 to remove the corresponding incorrect x-ray image from the model as represented by the table 703. For example, after selecting the portion of the path, the x-ray image may be highlighted in the GUI at the table 810 and the table 703. A selection may be made in the table 810 to uncheck and to remove the x-ray image from use in the model so that the x-ray image is also removed from the table 703.

Referring to FIG. 7, a sequential playing or providing of the x-ray images or pair of x-ray images (i.e., a movie mode) may be initiated in response to a selection of the movie mode icon 730. Further details with regard to the movie mode are described below.

Figure 9:
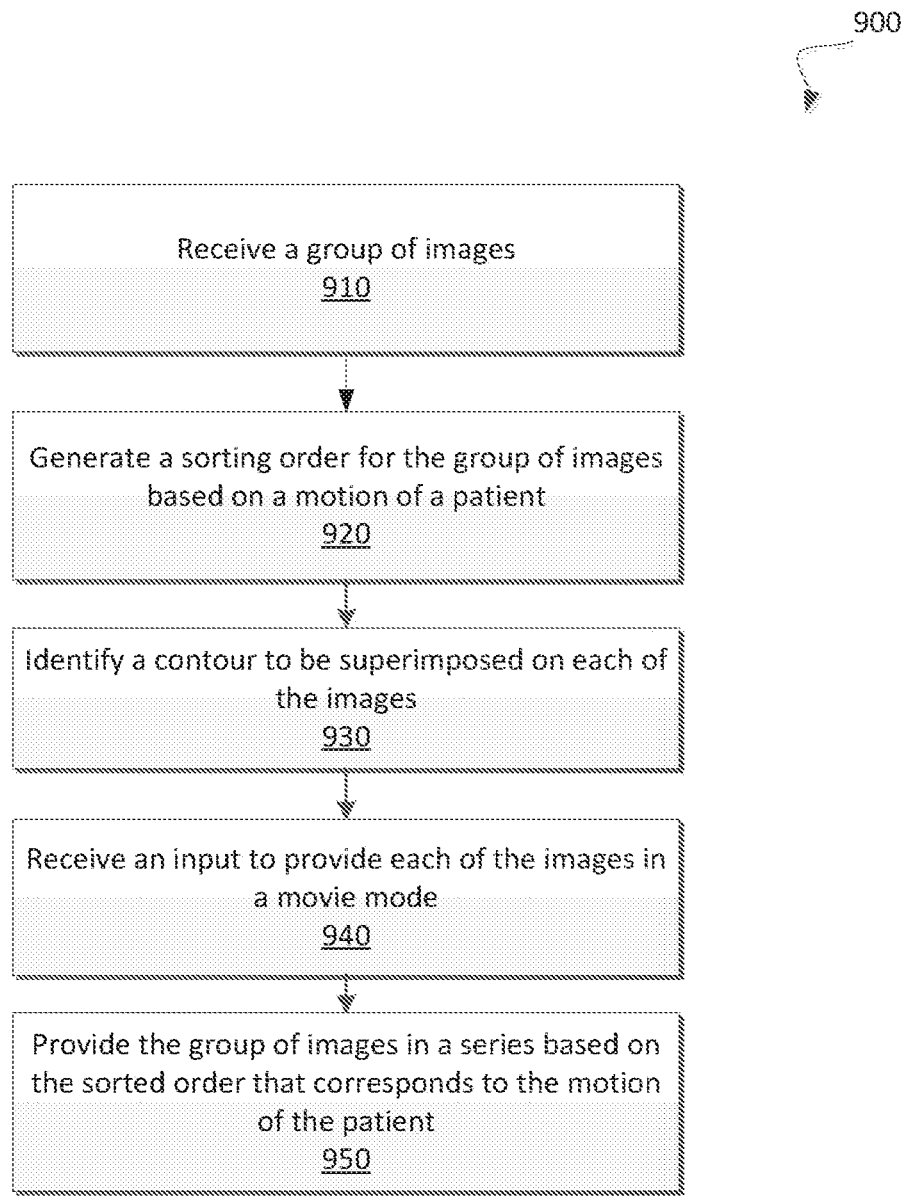
FIG. 9 illustrates an example method to provide a series of images with a superimposed contour in accordance with some embodiments.

FIG. 9 illustrates an example method 900 to provide a series of images with a superimposed contour. In general, the method 900 may be performed by processing logic that may comprise hardware (e.g., processing device, circuitry, dedicated logic, programmable logic, microcode, hardware of a device, integrated circuit, etc.), software (e.g., instructions run or executed on a processing device), or a combination thereof. In some embodiments, the method 900 is provided via the graphical user interface 700 or 800 of FIGS. 7 and 8.

As shown in FIG. 9, the method 900 may begin with the processing logic receiving a group of images (block 910). For example, a number of x-ray images that each are associated with correlation parameters that satisfy correlation parameter thresholds and that have been selected by a user to be included in the use by a model to identify a targeted region of a patient may be received. The processing logic may further generate a sorting order for the group of images based on a motion of the patient (block 920). In some embodiments, the sorting order may correspond to a respiratory order of the patient. Further details with regard to the sorting based on respiratory order are described in conjunction with FIG. 10. Furthermore, the processing logic may identify a contour on each of the series of images (block 930). The contour may represent a targeted region of the patient that is intended to receive radiation treatment. In some embodiments, the contour may be generated earlier during treatment planning for the patient and the contour that is earlier generated for each image may be included or superimposed on a display of the corresponding image. Thus, the contour is superimposed on each of the x-ray images that are used in the model. In alternative embodiments, another type of visual indicator may be used instead of the contour. For example, a crosshair may be used to identify the center of a detected tracking target or targeted region or a DRR may be overlaid on the x-ray image to show an alignment between the treatment plan and the x-ray image. Any type of visual indicator aside from a crosshair, contour, or DRR may be used and superimposed on each of the x-ray images. Subsequently, the processing logic may receive an input to initiate a playing of the group of images in a movie mode (block 940). For example, a selection from a GUI as described with regard to FIG. 7 may initiate a playing of the group of images in the sorted order that is based on the motion of the patient (i.e., the movie mode of the x-ray images). Subsequently, the processing logic may provide the group of images in a series based on the sorted order that corresponds to the motion of the patient (block 950). In an alternative embodiment, the playing of the group of images in the sorted order may be done automatically without user input.

As such, the x-ray images of a patient that are used by a model to identify a targeted region of the patient are sorted based on a respiratory order of the patient. The sorted x-ray images may be sequentially provided so that a progression of the x-ray images commences. As an example, the group of x-ray images may include fifteen x-ray images. In response to the initiating of the playing of the group of x-ray images, the group of x-ray images may be sorted based on a respiratory order of the patient and each of the x-ray images may be provided one after another in a progression so that each x-ray image may be provided without further input from the user. Each of the x-ray images may be provided for a predefined amount of time so that when the predefined amount of time has elapsed, the subsequent x-ray image in the sorted respiratory order may be provided.

Figure 10:
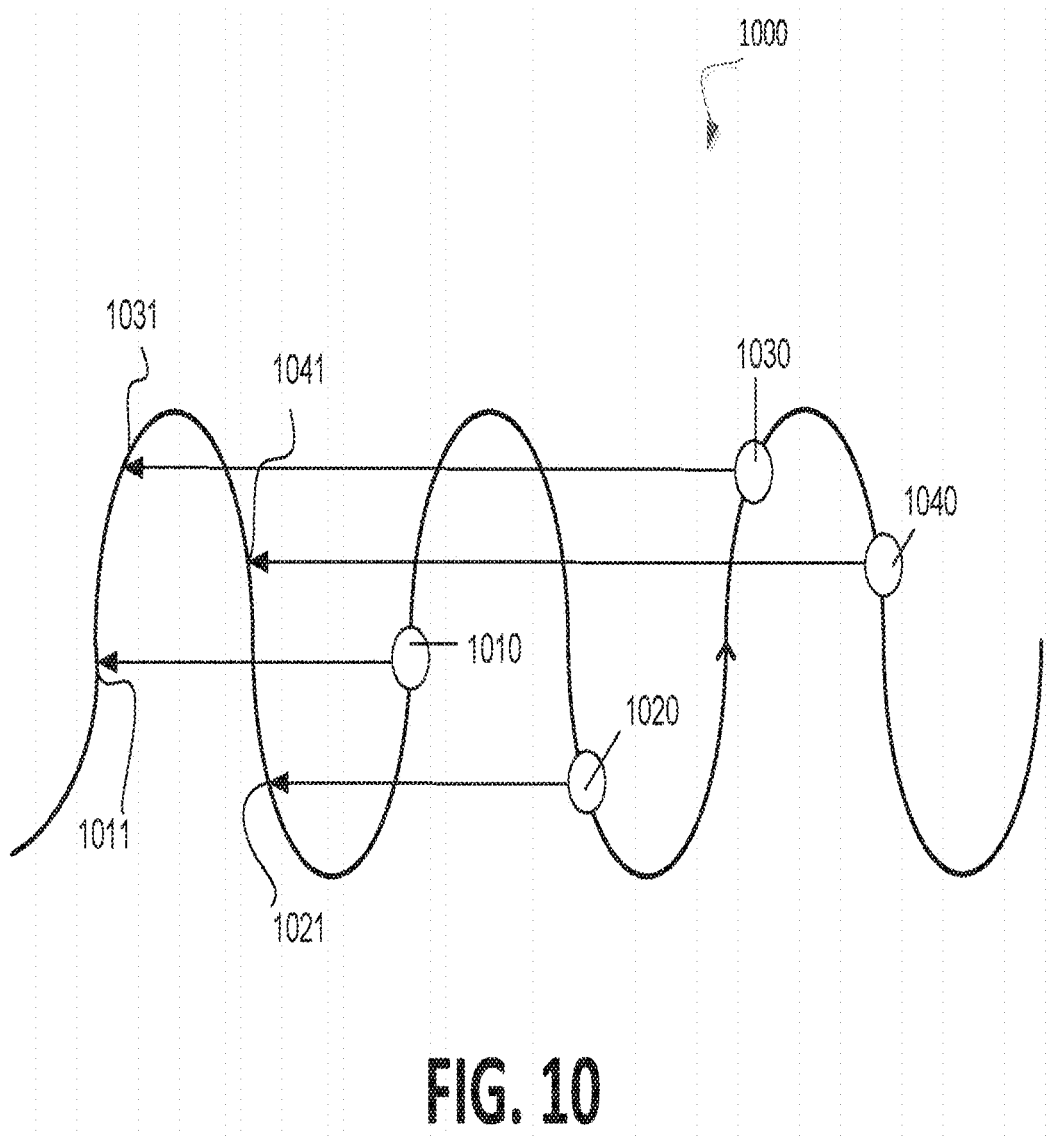
FIG. 10 illustrates the sorting of images to be in the series of images based on amplitude and phase associated with respiration of a patient in accordance with some embodiments of the present disclosure.

FIG. 10 illustrates the sorting 1000 of the group of images based on amplitude and phase associated with respiratory order of a patient. In general, the sorting 1000 may be based on x-ray images that have satisfied correlation parameter thresholds and that have been selected by a user to be used in a model to identify a targeted region of a patient.

As shown in FIG. 10, a first x-ray image 1010 may be in the group of x-ray images used in the model. The first x-ray image 1010 may be identified as being associated with a position or amplitude during an upwards phase of the respiratory motion of the patient. As such, the first x-ray image 1010 may be sorted to a position 1011. The second x-ray image 1020 may be associated with a second position or amplitude during a downwards phase of the respiratory motion of the patient. As such, the second x-ray image 1020 may be sorted to a second position 1021 based on the amplitude and downwards phase of its corresponding location. Similarly, the third x-ray image 1030 may be sorted to a position 1031 and the fourth x-ray image 1040 may be sorted to a position 1041, each based on the amplitude and respiratory phase of its corresponding location. In some embodiments, the first x-ray image 1010 may be captured or taken of a patient first (e.g., has the earliest age as previously described), the second x-ray image 1020 may be taken second, the third x-ray image 1030 may be taken third, and the fourth x-ray image 1040 may be taken fourth. Thus, the group of images may be sorted so that when the movie mode or playing of the x-ray images is initiated, the first x-ray image 1010 is provided first, followed by the third x-ray image 1030, fourth x-ray image 1040, and then the third x-ray image 1030 as the movie mode may provide the x-ray images in a sequence based on the sorted order as opposed to an age or when the x-ray images were taken.

Thus, the x-ray images 1010, 1020, 103, and 1040 may be sorted to positions within the respiratory order or motion of the patient. For example, the x-ray image 1010 may be sorted to a first position in the respiratory order and the x-ray image 1020 may be sorted to a final position in the respiratory order. Furthermore, the x-ray images 1030 and 1040 may be sorted to intermediate positions in the respiratory order that are between the first position and the final position. In some embodiments, the respiratory order may correspond to one period of a waveform that represents the upwards motion of a patient during a respiratory motion and a downwards motion of the patient during the respiration motion. The x-ray image that is sorted to the earliest point in the period may be the first location and the x-ray image that is sorted the latest point in the period of the waveform may be the final location in the period that represents the respiratory order or motion. The x-ray images that are between the earliest and latest point may be considered to be intermediate points.

Figure 11:
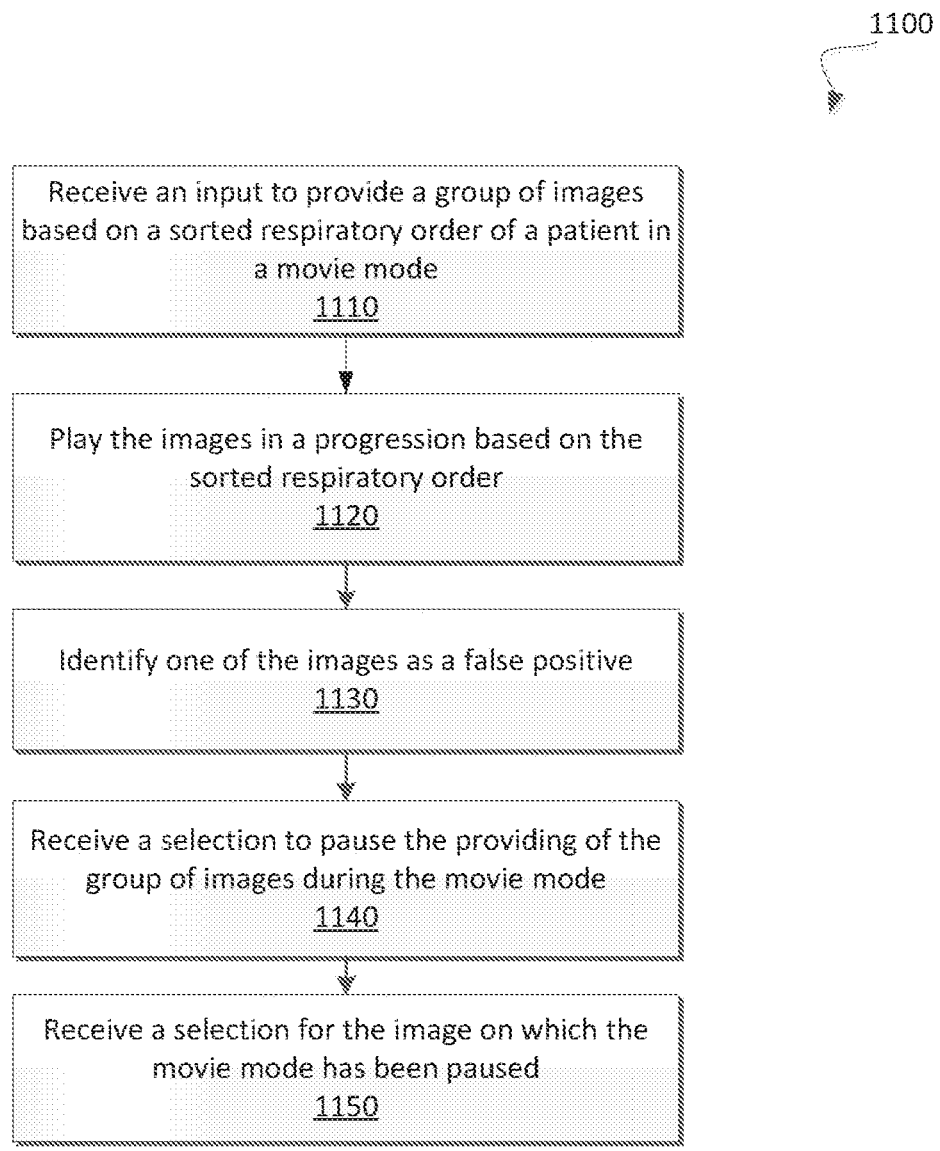
FIG. 11 is a flow diagram of an example method to provide a series of images based on a modification to an image in the series of images in accordance with some embodiments.

FIG. 11 is a flow diagram of an example method 100 to provide a group of images and identify a false positive image. In general, the method 1100 may be performed by processing logic that may comprise hardware (e.g., processing device, circuitry, dedicated logic, programmable logic, microcode, hardware of a device, integrated circuit, etc.), software (e.g., instructions run or executed on a processing device), or a combination thereof. In some embodiments, the method 1100 is provided via the graphical user interface 700 or 800 of FIGS. 7 and 8.

As shown in FIG. 11, the method 1100 may begin with the processing logic receiving an input to provide a group of images based on a sorted respiratory order of a patient (block 1110). For example, a selection of a GUI element as described with regard to FIG. 7 may be received. In response to the input, images from the group of images may be provided in a progression that is based on the sorted respiratory order (block 1120). The location of the tumor of the patient may be more easily ascertainable around healthy tissue and bone structure during the playing of the images. As the images from the group of images are provided and progressed through, the processing logic may identify one of the images as a false positive during the playing of the images (block 1130). For example, a selection may be provided by a user via the GUI of FIG. 7 or 8 based on the contour and the tumor where the contour for a particular image is out of an expected order for the image. Further details with regard to identifying a false positive during the providing of the x-ray images in a sequence are described in conjunction with FIGS. 12A-C. In some embodiments, the false positive may be identified when the contour for the particular image does not contain the tumor of the patient in the x-ray image. In the same or alternative embodiments, an indication may be provided in the GUI when a false positive is identified. For example, a user may provide the indication of the false positive. The processing logic may further receive a selection to pause the providing of the images in the sequence (block 1140). For example, another selection may be provided via the GUI of FIG. 7 or 8 to stop the playing of the x-ray images during the movie mode. Subsequently, the processing logic may receive a selection for the image on which the playing of the group of images has stopped or been paused during the movie mode (block 1150). The selection may be to remove the image for which the false positive is identified from the group of images that are used by the model.

As such, a movie mode for the group of images may be provided so that the group of images are sorted based on a respiratory order and are sequentially played in a graphical user interface. The location and movement of the tumor may be more easily ascertained by the playing of the group of images in the movie mode. Furthermore, the movement of the contour and tracking the contour over the location of the tumor during the respiratory order of the patient may be identified so that if the contour is out of an expected order, then the corresponding image may be identified as a false positive and may be removed from use in the model that is used to identify the targeted region that will receive the radiation treatment.

Figure 12A:
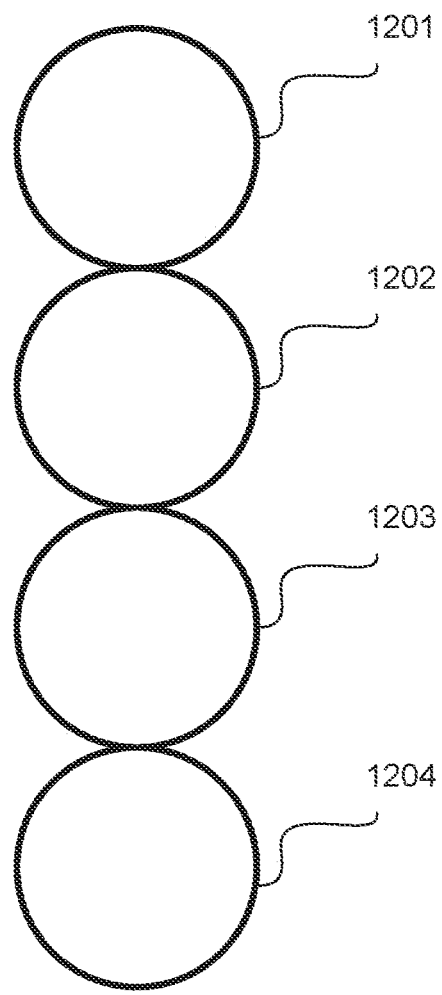
FIG. 12A illustrates an example of a moving of the contour during a playing of the group of images in a movie mode in accordance with some embodiments.

FIG. 12A illustrates an example of a moving of the contour during the playing of the group of images. In general, the moving of the contour may be provided in response to a selection to initiate a movie mode for a group of images that are provided by a graphical user interface (e.g., graphical user interface 700).

As shown in FIG. 12A, a series of contours may be provided where each contour represents a location of a contour that has been superimposed on a corresponding x-ray image. As the x-ray images are played in the movie mode, the contours for each x-ray image may move locations. For example, as shown, a first contour 1201 may be at a first location, a second contour 1202 may be at a second location, a third contour 1203 may be at a third location, and a fourth contour 1204 may be at a fourth location. The locations of the first through fourth contours 1201 through 1204 may be in an expected placement or path. For example, the path may be approximately a straight line, an oval, or other such geometric shape. As shown in FIG. 12A, the contours 1201-1204 are in a straight line. As such, an indication may be provided that there is not a false positive with the contours or x-ray images and the model may be appropriate for providing radiation treatment for the targeted region. In some embodiments, instead of a straight line, an indication that there is not a false positive may correspond to the contours 1201-1204 incrementally moving within a particular motion pattern. For example, when the contours 1201-1204 may move within a curve, an ellipse, or any other logical sequence or pattern in an incremental fashion, then there may not be a false positive.

Figure 12B:
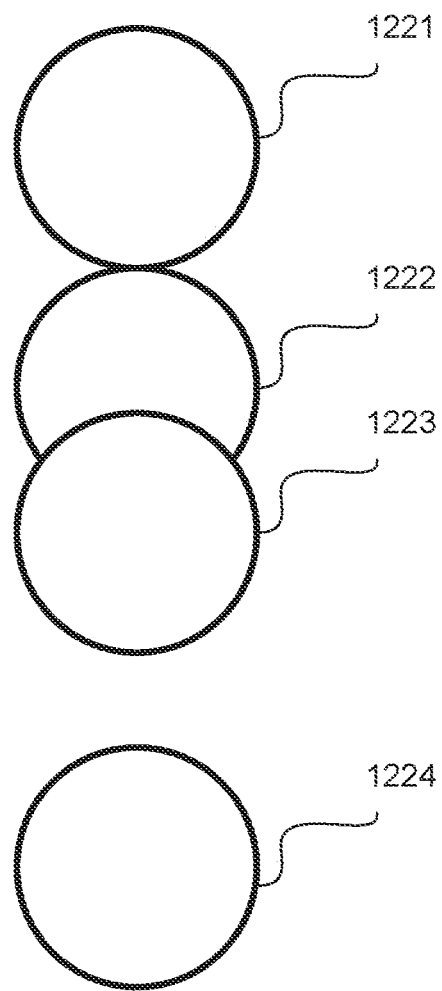
FIG. 12B illustrates an example of the moving of the contour during the playing of the group of images in a movie mode that may be associated with an error in accordance with some embodiments.

FIG. 12B illustrates an example of a moving of the contour during the playing of the group of images that is associated with a false positive. In general, the moving of the contour may be provided in response to a selection to initiate a movie mode for a group of images that are provided by a graphical user interface (e.g., graphical user interface 700).

As shown in FIG. 12B, the series of contours may include a first contour 1221 that is provided first in an x-ray image in movie mode, second contour 1222 that is provided second, third contour 1223 that is provided third, and a fourth contour 1224 that is provided fourth. During the playing of the group of images with the superimposed contours during movie mode, the first contour 1221 to second contour 1222 may be in a particular direction (e.g., a downwards motion) and the fourth contour 1224 may be further in the same direction (e.g., also in a downwards motion). Thus, each of the first contour 1221, second contour 1222, and fourth contour 1224 may be in locations that correspond to a movement of the contour between x-ray images in the same direction. However, the third contour 1223 may be located at a position that is the opposite (e.g., in an upwards motion) from the first contour 1221, second contour 1222, and fourth contour 1224. For example, the location of the third contour 1223 is after the location of the second contour 1222 and before the location of the fourth contour 1224. As such, with a jump, or a discontinuous motion, associated with the third contour 1223, an identification may be provided that the x-ray image with the superimposed third contour 1223 is a false positive.

Figure 12C:
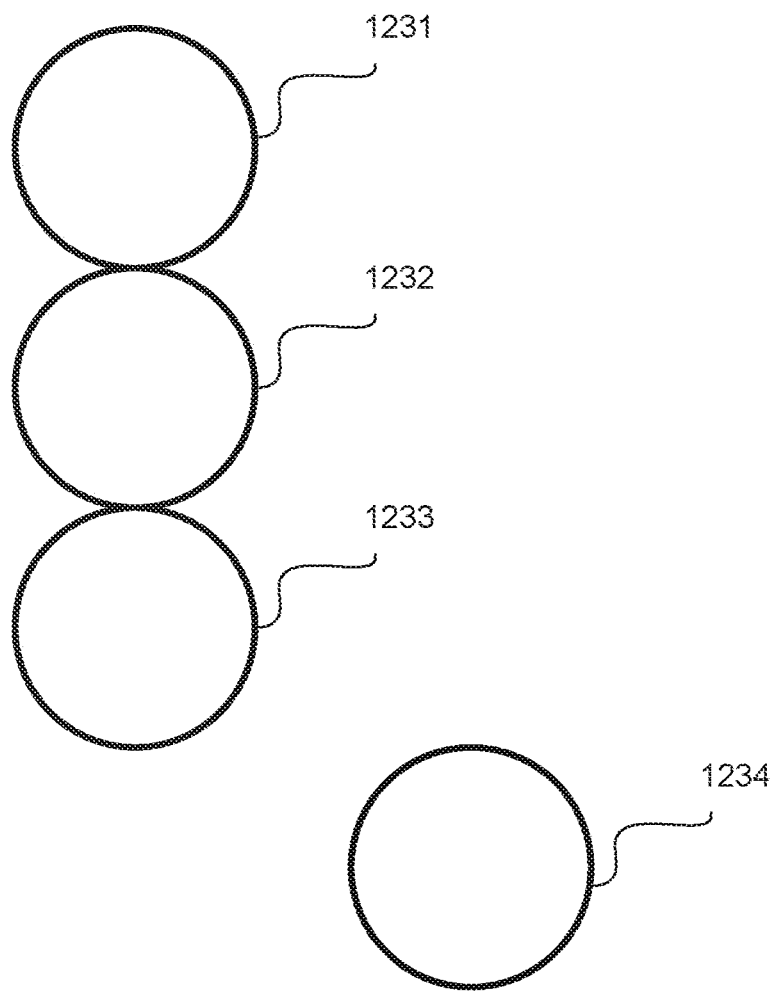
FIG. 12C illustrates another example of the moving of the contour during the playing of the group of images in a movie mode that may be associated with another error in accordance with some embodiments.

FIG. 12C illustrates another example of a moving of the contour during the playing of the group of images that is associated with a false positive. In general, the moving of the contour may be provided by a graphical user interface 700 of FIG. 7.

As shown in FIG. 12C, the series of contours may include a first contour 1231, second contour 1232, third contour 1233, and a fourth contour 1234. The first contour 1231, second contour 1232, and third contour 1233 may be within a similar path (e.g., a line). However, as shown, the fourth contour 1234 may be outside of the expected path (e.g., not at a location along the line). As such, an identification may be provided that the x-ray image with the superimposed fourth contour 1234 is a false positive.

Figure 13:
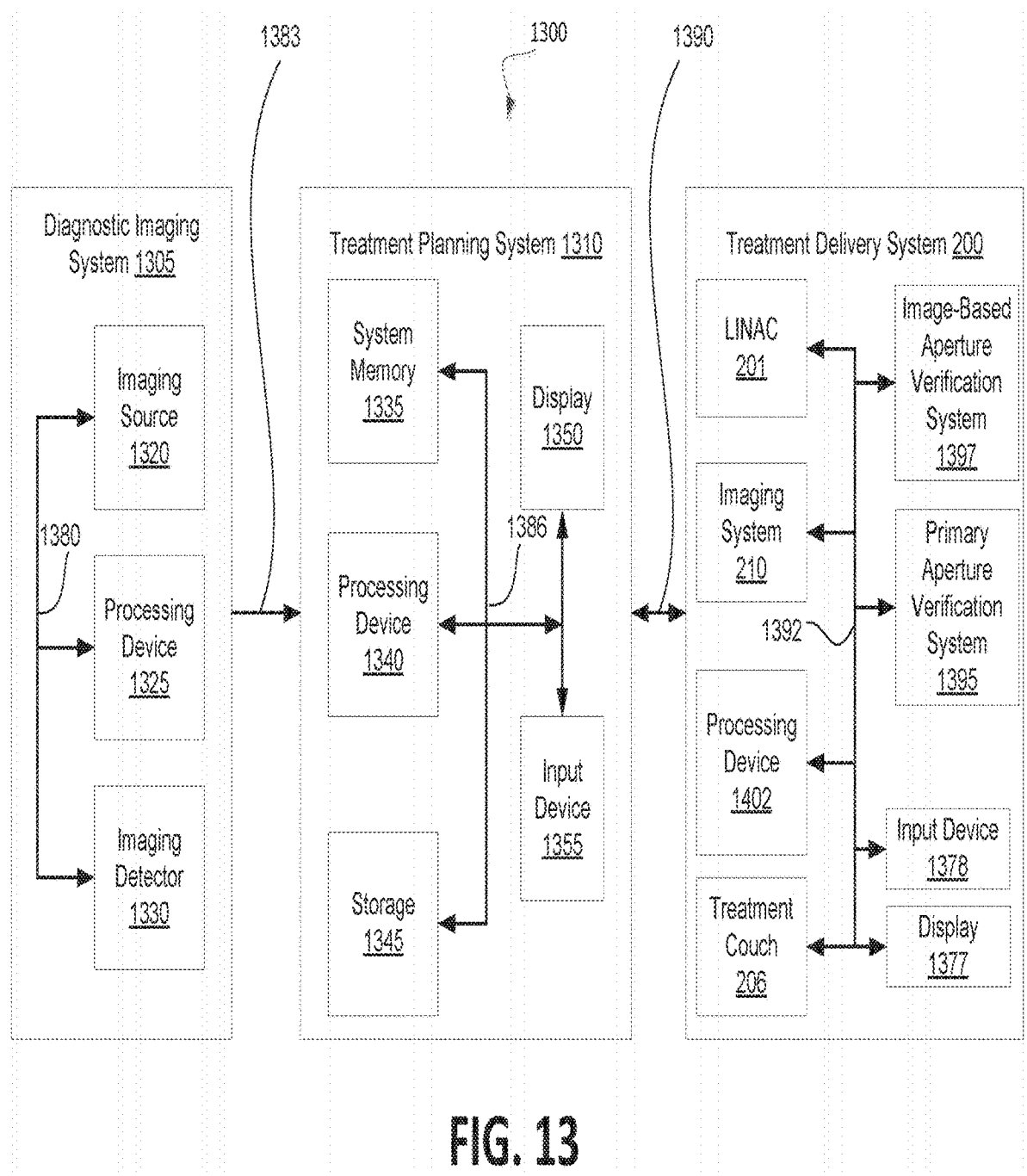
FIG. 13 illustrates a system that may be used in the generating of a treatment plan and the performing of radiation treatment in accordance with some embodiments of the present disclosure.

FIG. 13 illustrates a system that may be used in generating a treatment plan and the performing of radiation treatment. These systems may be used to perform, for example, the methods described above. As described below and illustrated in FIG. 13, a system 1300 may include a diagnostic imaging system 1305, a treatment planning system 1310, the treatment delivery system 200 as described with regard to FIG. 2, and a motion detecting system (not shown). In one embodiment, the diagnostic imaging system 1305 and the motion detecting system are combined into a single unit.

Diagnostic imaging system 1305 may be any system capable of producing medical diagnostic images of a patient that may be used for subsequent medical diagnosis, treatment planning, treatment simulation and/or treatment delivery. For example, diagnostic imaging system 1305 may be a computed tomography (CT) system, a magnetic resonance imaging (MRI) system, a positron emission tomography (PET) system, or the like. For ease of discussion, diagnostic imaging system 1305 may be discussed below at times in relation to an x-ray imaging modality. However, other imaging modalities such as those above may also be used.

In one embodiment, diagnostic imaging system 1305 includes an imaging source 1320 to generate an imaging beam (e.g., x-rays) and an imaging detector 1330 to detect and receive the imaging beam generated by imaging source 1320.

The imaging source 1320 and the imaging detector 1330 may be coupled to a processing device 1325 to control the imaging operation and process image data. In one embodiment, diagnostic imaging system 1305 may receive imaging commands from treatment delivery system 200.

Diagnostic imaging system 1305 includes a bus or other means 1380 for transferring data and commands among processing device 1325, imaging source 1320 and imaging detector 1330. Processing device 1325 may include one or more general-purpose processors (e.g., a microprocessor), special purpose processor such as a digital signal processor (DSP) or other type of device such as a controller or field programmable gate array (FPGA). Processing device 1325 may also include other components (not shown) such as memory, storage devices, network adapters and the like. Processing device 1325 may be configured to generate digital diagnostic images in a standard format, such as the DICOM (Digital Imaging and Communications in Medicine) format, for example. In other embodiments, processing device 1325 may generate other standard or non-standard digital image formats. Processing device 1325 may transmit diagnostic image files (e.g., the aforementioned DICOM formatted files) to treatment delivery system 200 over a data link 1383, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present disclosure to diagnose or treat a patient despite the existence of a physical separation between the system user and the patient.

Treatment delivery system 200 includes a therapeutic and/or surgical radiation source such as the LINAC 201 to administer a prescribed radiation dose to a target volume in conformance with a treatment plan. Treatment delivery system 200 may also include a processing device 1402 to control radiation source 201, image-based aperture verification system 1397, primary aperture verification system 1395, receive and process data from an imaging system 210, and control a patient support device such as a treatment couch 206. Alternatively or additionally, image-based aperture verification system 1397 may include its own processing device, which may perform operations described herein. Processing device 1402 may be configured to register 2D radiographic images received from diagnostic imaging system 1305, from one or more projections, with digitally reconstructed radiographs (DRRs) generated by processing device 1325 in diagnostic imaging system 1305 and/or DRRs generated by processing device 1340 in treatment planning system 1310. Processing device 1402 may include one or more general-purpose processors (e.g., a microprocessor), special purpose processor such as a digital signal processor (DSP) or other type of device such as a controller or field programmable gate array (FPGA). Similarly, a processing device of image-based aperture verification system 1397 may include one or more general-purpose processors (e.g., a microprocessor), special purpose processor such as a digital signal processor (DSP) or other type of device such as a controller or field programmable gate array (FPGA). Processing device 1402 and/or image based aperture verification system 1397 may also include other components (not shown) such as memory, storage devices, network adapters and the like.

In one embodiment, processing device 1402 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Processing device 1402 may also be associated with a storage device, representing one or more storage devices (e.g., a magnetic disk drive or optical disk drive) for storing information and instructions. The storage device may be used for storing instructions for performing the treatment delivery steps discussed herein. Processing device 1402 may be coupled to radiation source 201 and treatment couch 206 by a bus 1392 or other type of control and communication interface.

Processing device 1402 may implement methods to manage timing of diagnostic x-ray imaging in order to maintain alignment of a target with a radiation treatment beam delivered by the radiation source 201.

In one embodiment, the treatment delivery system 200 includes an input device 1378 and a display 1377 connected with processing device 1402 via bus 1392. The display 1377 may provide the GUIs 700 and/or 800. The display 1377 can also show trend data that identifies a rate of target movement (e.g., a rate of movement of a target volume that is under treatment). The display can also show a current radiation exposure of a patient and a projected radiation exposure for the patient. The input device 1378 can enable a clinician to adjust parameters of a treatment delivery plan during treatment.

Treatment planning system 1310 includes a processing device 1340 to generate and modify treatment plans and/or simulation plans. Processing device 1340 may represent one or more general-purpose processors (e.g., a microprocessor), special purpose processor such as a digital signal processor (DSP) or other type of device such as a controller or field programmable gate array (FPGA). Processing device 1340 may be configured to execute instructions for performing treatment planning operations.

Treatment planning system 1310 may also include system memory 1335 that may include a random access memory (RAM), or other dynamic storage devices, coupled to processing device 1340 by bus 1386, for storing information and instructions to be executed by processing device 1340. System memory 1335 also may be used for storing temporary variables or other intermediate information during execution of instructions by processing device 1340. System memory 1335 may also include a read only memory (ROM) and/or other static storage device coupled to bus 1386 for storing static information and instructions for processing device 1340.

Treatment planning system 1310 may also include storage 1345, representing one or more storage devices (e.g., a magnetic disk drive or optical disk drive) coupled to bus 1386 for storing information and instructions. Storage 1345 may be used for storing instructions for performing treatment planning.

Processing device 1340 may also be coupled to a display device 1350, such as a cathode ray tube (CRT) or liquid crystal display (LCD), for displaying information (e.g., a 2D or 3D representation of a volume of interest (VOI)) to a user. An input device 1355, such as a keyboard, may be coupled to processing device 1340 for communicating information and/or command selections to processing device 1340. One or more other user input devices (e.g., a mouse, a trackball or cursor direction keys) may also be used to communicate directional information, to select commands for processing device 1340 and to control cursor movements on display 1350.

Treatment planning system 1310 may share its database (e.g., data stored in storage 1345) with a treatment delivery system, such as treatment delivery system 200, so that it may not be necessary to export from the treatment planning system prior to treatment delivery. Treatment planning system 1310 may be linked to treatment delivery system 200 via a data link 1390, which may be a direct link, a LAN link or a WAN link.

It should be noted that when data links 1383 and 1390 are implemented as LAN or WAN connections, any of diagnostic imaging system 1305, treatment planning system 1310 and/or treatment delivery system 200 may be in decentralized locations such that the systems may be physically remote from each other. Alternatively, any of diagnostic imaging system 1305, treatment planning system 1310, and/or treatment delivery system 200 may be integrated with each other in one or more systems.

Figure 14:
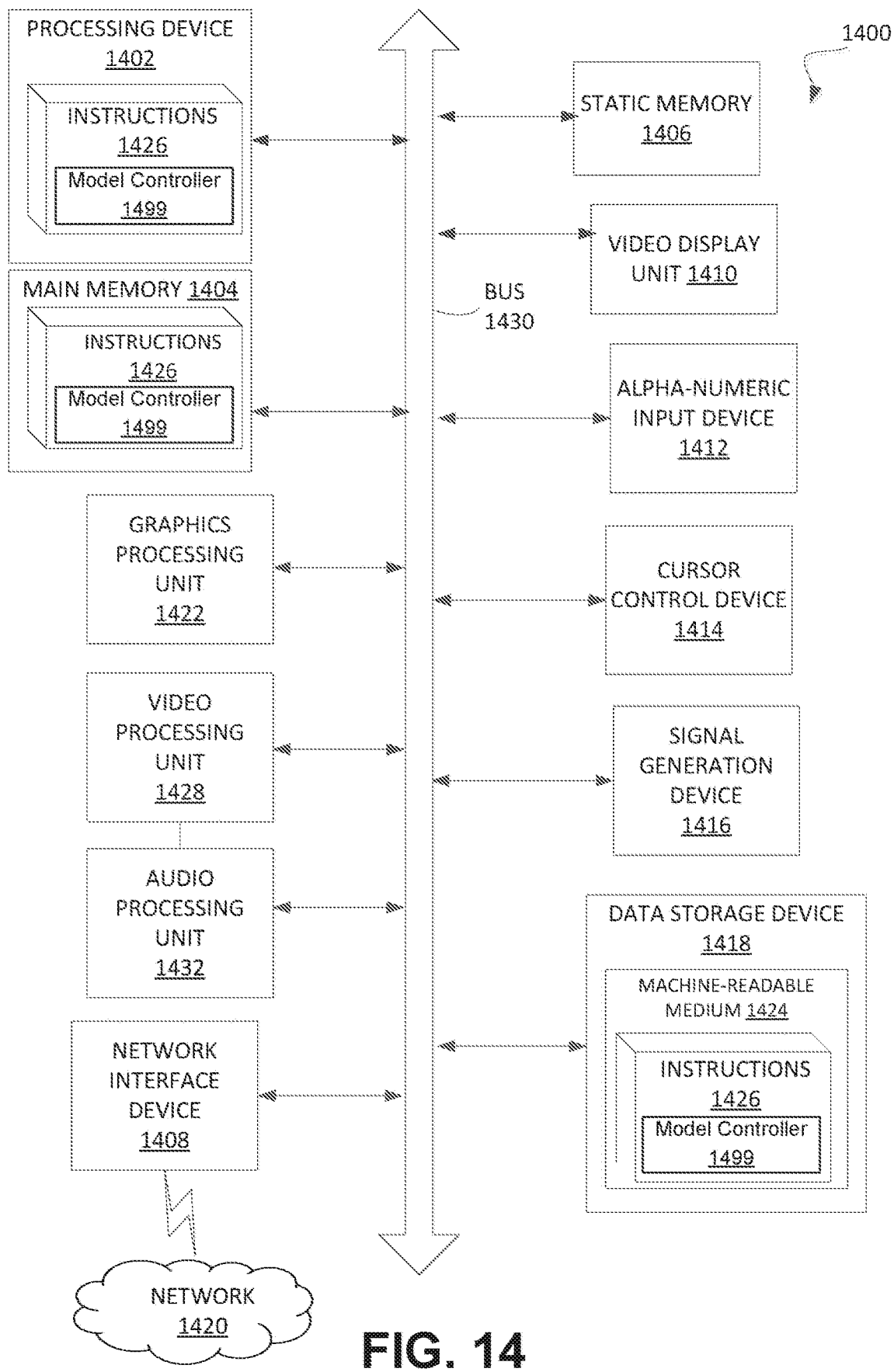
FIG. 14 illustrates a block diagram of an embodiment of a computer system in which some embodiments of the disclosure may operate.

FIG. 14 illustrates an example machine of a computer system 1400 within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 1400 includes a processing device 1402, a main memory 1404 (e.g., read-only memory (ROM), flash memory, dynamic random access memory (DRAM) such as synchronous DRAM (SDRAM) or Rambus DRAM (RDRAM), etc.), a static memory 1406 (e.g., flash memory, static random access memory (SRAM), etc.), and a data storage device 1418, which communicate with each other via a bus 1430.

Processing device 1402 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1402 may also be one or more special-purpose processing devices such as an application specific integrated circuit (ASIC), a field programmable gate array (FPGA), a digital signal processor (DSP), network processor, or the like. The processing device 1402 is configured to execute instructions 1426 for performing the operations and steps discussed herein.

The computer system 1400 may further include a network interface device 1408 to communicate over the network 1420. The computer system 1400 also may include a video display unit 1410 (e.g., a liquid crystal display (LCD) or a cathode ray tube (CRT)), an alphanumeric input device 1412 (e.g., a keyboard), a cursor control device 1414 (e.g., a mouse), a graphics processing unit 1422, a signal generation device 1416 (e.g., a speaker), graphics processing unit 1422, video processing unit 1428, and audio processing unit 1432.

The data storage device 1418 may include a machine-readable storage medium 1424 (also known as a computer-readable medium) on which is stored one or more sets of instructions or software 1426 embodying any one or more of the methodologies or functions described herein. The instructions 1426 may also reside, completely or at least partially, within the main memory 1404 and/or within the processing device 1402 during execution thereof by the computer system 1400, the main memory 1404 and the processing device 1402 also constituting machine-readable storage media.

In one implementation, the instructions 1426 include instructions for a model controller 499 to implement functionality corresponding to the disclosure herein. While the machine-readable storage medium 1424 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A method comprising:
   receiving a plurality of images that are associated with an identification of a tracking target of a patient to receive radiation treatment;
   sorting the plurality of images into a sequence based on a motion of the patient, wherein the motion comprises a respiratory motion of the patient;
   receiving an input selection, via a graphical user interface (GUI), to provide the sorted plurality of images in a movie mode, wherein each of the sorted images is provided in the sequence for a defined amount of time;
   receiving an indication that an image of the sorted plurality of images corresponds to a false positive during the providing of the plurality of images, wherein the false positive is based on a corresponding visual indicator of the image being at a position that deviates from a path associated with other visual indicators of the plurality of images;
   causing display of, by a processing device, the sorted plurality of images, in the sequence, that is based on the motion of the patient in response to the input selection;
   providing a contour on each of the sorted images to represent the treatment target of the patient that has been identified;
   providing, by a processing device, a visual indicator within the GUI that is superimposed on each of the sorted images to represent the tracking target of the patient that has been identified in each of the sorted plurality of images;
   receiving another selection, via the GUI, to remove at least one image from being used to identify the tracking target of the patient; and
   identifying the tracking target of the patient without the at least one removed image.

2. The method of claim 1, wherein the sorting of the plurality of images into the sequence based on the motion of the patient is in view of a phase and an amplitude associated with the respiratory motion of the patient when each of the plurality of images was taken of the patient.

3. The method of claim 1, further comprising:
   receiving an input selection via the GUI to provide the sorted plurality of images in the sequence that is based on the motion of the patient, wherein the providing of the sorted plurality of images is in response to the input selection.

4. The method of claim 1, wherein the plurality of images are x-ray images of the patient.

5. A system comprising:
   a memory to store a plurality of images that are associated with an identification of a tracking target of a patient to receive radiation treatment; and
   a processing device operatively coupled with the memory to:
   receive the plurality of images;
   sort the plurality of images into a sequence based on a motion of the patient,
   wherein the motion comprises a respiratory motion of the patient;
   receive an input selection, via a graphical user interface (GUI), to provide the sorted plurality of images in a movie mode, wherein each of the sorted images is provided in the sequence for a defined amount of time;
   receive an indication that an image of the sorted plurality of images corresponds to a false positive during the providing of the plurality of images, wherein the false positive is based on a corresponding visual indicator of the image being at a position that deviates from a path associated with other visual indicators of the plurality of images;
   cause display of the sorted plurality of images, in the sequence, that is based on the motion of the patient in response to the input selection;
   provide a contour on each of the sorted images to represent the treatment target of the patient that has been identified;
   provide a visual indicator within the GUI that is superimposed on each of the sorted images to represent the tracking target of the patient that has been identified in each of the sorted plurality of images;
   receive another selection, via the GUI, to remove at least one image from being used to identify the tracking target of the patient; and
   identify the tracking target of the patient without the at least one removed image.

6. The system of claim 5, wherein the sorting of the plurality of images into the sequence based on the motion of the patient is in view of a phase and an amplitude associated with the respiratory motion of the patient when each of the plurality of images was taken of the patient.

7. The system of claim 5, wherein the processing device is further to:
   receive an input selection via the graphical user interface to provide the sorted plurality of images in the sequence that is based on the motion of the patient, wherein the providing of the sorted plurality of images is in response to the input selection.

8. The system of claim 5, wherein the plurality of images are x-ray images of the patient.

9. A non-transitory computer readable medium comprising instructions that, when executed by a processing device, cause the processing device to:
   receive a plurality of images that are associated with an identification of a tracking target of a patient to receive radiation treatment;
   sort the plurality of images into a sequence based on a motion of the patient, wherein the motion comprises a respiratory motion of the patient;

receive an input selection, via a graphical user interface (GUI), to provide the sorted plurality of images in a movie mode, wherein each of the sorted images is provided in the sequence for a defined amount of time;

receive an indication that an image of the sorted plurality of images corresponds to a false positive during the providing of the plurality of images, wherein the false positive is based on a corresponding visual indicator of the image being at a position that deviates from a path associated with other visual indicators of the plurality of images;

cause display of the sorted plurality of images, in the sequence, that is based on the motion of the patient in response to the input selection;

provide a contour on each of the sorted images to represent the treatment target of the patient that has been identified;

provide a visual indicator within the GUI that is superimposed on each of the sorted images to represent the tracking target of the patient that has been identified in each of the sorted plurality of images;

receive another selection, via the GUI, to remove at least one image from being used to identify the tracking target of the patient; and identify the tracking target of the patient without the at least one removed image.

10. The non-transitory computer readable medium of claim 9, wherein the sorting of the plurality of images into the sequence based on the motion of the patient is in view of a phase and an amplitude associated with the respiratory motion of the patient when each of the plurality of images was taken of the patient.

11. The non-transitory computer readable medium of claim 9, wherein the processing device is further to:

receive an input selection via the GUI to provide the sorted plurality of images in the sequence that is based on the motion of the patient, wherein the providing of the sequence is in response to the input selection.

12. The non-transitory computer readable medium of claim 9, wherein the plurality of images are x-ray images of the patient.

* * * * *